(12) United States Patent
Bentivegna et al.

(10) Patent No.: US 11,810,165 B1
(45) Date of Patent: Nov. 7, 2023

(54) COMPUTERIZED TIME-SERIES ANALYSIS FOR INFERENCE OF CORRELATED INPUT MODIFICATIONS

(71) Applicant: Cigna Intellectual Property, Inc., Wilmington, DE (US)

(72) Inventors: Joseph Bentivegna, New York, NY (US); Itzchak J. Palka, New York, NY (US); Eetai Ben-Sasson, Brooklyn, NY (US); Vivek Pandey, North Arlington, NJ (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 391 days.

(21) Appl. No.: 17/123,937

(22) Filed: Dec. 16, 2020

Related U.S. Application Data

(63) Continuation of application No. 17/123,855, filed on Dec. 16, 2020.

(51) Int. Cl.
  *G06Q 30/04* (2012.01)
  *G16H 10/00* (2018.01)

(52) U.S. Cl.
  CPC ............. *G06Q 30/04* (2013.01); *G16H 10/00* (2018.01)

(58) Field of Classification Search
  CPC ... G06Q 10/10; G06Q 30/04; G06Q 50/20–26
  See application file for complete search history.

(56) References Cited

U.S. PATENT DOCUMENTS

| | | | |
|---|---|---|---|
| 7,995,991 B2 | 8/2011 | Johnson | |
| 9,015,054 B2 | 4/2015 | Lara | |
| 9,514,387 B2 | 12/2016 | Eaton | |
| 9,569,804 B2 | 2/2017 | Stein | |
| 10,298,749 B2 | 5/2019 | Mumick | |
| 10,842,378 B2 | 11/2020 | Verma | |
| 2007/0162367 A1* | 7/2007 | Smith | G06Q 40/00 705/35 |
| 2008/0021715 A1* | 1/2008 | Alderoty | G06Q 30/00 705/30 |

(Continued)

OTHER PUBLICATIONS

Lapointe, RevCycle Intelligence, The Role of the Hospital Chargemaster in Revenue Cycle Management, https://revcycleintelligence.com/features/the-role-of-the-hospital-chargemaster-in-revenue-cycle-management, accessed as early as May 14, 2020.

(Continued)

*Primary Examiner* — Neal Sereboff
(74) *Attorney, Agent, or Firm* — Miller Johnson

(57) ABSTRACT

A computerized analysis system includes a data retrieval module, a spike filter module, a chargemaster analysis module, and an alert module. The data retrieval module is configured to retrieve claimline data for a period of time from an input data store. The claimline data includes billing codes and prices of the billing codes associated with a provider. The spike filter module is configured to flag and filter price spikes in the claimline data. The chargemaster analysis module is configured to determine whether a changepoint exists in the billing codes in the claimline data. The chargemaster analysis module is configured to identify a chargemaster increase for the provider in response to a statistical parameter of changepoints exceeding a threshold. The alert module is configured to, in response to identification of a chargemaster increase, publish an alert that a chargemaster increase has occurred for the provider.

20 Claims, 23 Drawing Sheets

(56) References Cited

U.S. PATENT DOCUMENTS

| | | |
|---|---|---|
| 2010/0174627 A1 | 7/2010 | Daniels |
| 2011/0112851 A1 | 5/2011 | Poley |
| 2011/0251951 A1 | 10/2011 | Kolkowitz |
| 2014/0279318 A1 | 9/2014 | Friedman |
| 2014/0379303 A1 | 12/2014 | Chandrashekaraiah |
| 2015/0186972 A1* | 7/2015 | Selvam ............. G06Q 30/0202 |
| | | 705/26.61 |
| 2015/0278458 A1 | 10/2015 | Omidi |
| 2015/0332292 A1* | 11/2015 | Unser ................... G06Q 30/02 |
| | | 705/7.31 |
| 2016/0350501 A1 | 12/2016 | Rothschild |
| 2018/0239870 A1 | 8/2018 | Goldman |
| 2019/0304021 A1 | 10/2019 | Rutherford |
| 2019/0325455 A1 | 10/2019 | Hunt |
| 2019/0339285 A1 | 11/2019 | Stumbo |
| 2021/0158404 A1* | 5/2021 | Bansal ............... G06Q 30/0276 |

\* cited by examiner

Regional Medical Center
Regional Medical Center

Provider Findings
| | |
|---|---|
| Detected CMI % Increase | 6.24% |
| Data Cleanliness | 5/5 |
| Date of Surveillance | 08/01/2020 |
| Detected CMI Date | 10/02/2019 |

Contract Information
| | |
|---|---|
| CPL | 0.00% |
| % OP POC | 100.00% |
| Current Contract Effective Date | 10/01/2019 |
| Next Contract Effective Date | 10/01/2019 |

Since Last Detected CMI
| | |
|---|---|
| Total Charges | $124,563,788 |
| Total Charge Change Impact | $7,340,359 |
| Allowed to Enforce | $7,340,359 |
| % of Codes Included in Aggregation | 59.00% |

Detection Details
| | |
|---|---|
| Claimlines | 43,847 |
| Valid Changepoints | 996 |
| Spikes | 991 |
| Units | 182,292 |

Service Categories
Click on a service category to view more details at the sub-category level.

| Service Category | Allowed to Enforce | CMI % Increase | Total Charge Change Impact | Total Charges Since Last CMI | Units Since Last CMI |
|---|---|---|---|---|---|
| Emergency Room (All Le...) | $1,815,911 | 6.99% | $1,815,911 | $24,2244,799 | 10,024 |
| Cat Scan | $1,132,300 | 10.02% | $1,132,300 | $14,477,051 | 2,967 |
| Observation Unit | $1,008,006 | 21.62% | $1,008,006 | $3,195,620 | 1,213 |
| Nuclear Medicine | $657,416 | 12.74% | $657,416 | $6,611,926 | 2,556 |

*FIG. 11*

1200 — Browser window with tabs: Opportunity Detection ×, Performance Monitoring ×, +
URL: https://contractmodeling.crxlabs.net/chargemaster/surveillance/4477823/08-01-20

Performance Monitoring  Chargemaster

Regional Medical Center  ‹ Emergency Room (All Levels)

Regional Medical Center

[Definitions]  [Download]

1202 — Emergency Room (All Levels)

| Category Findings | |
|---|---|
| Detected CMI % Increase | 6.99% |
| Data Cleanliness | 5/5 |
| Date of Surveillance | 08/01/2020 |
| Detected CMI Date | 10/02/2019 |

1204 — Since Last Detected CMI

| | |
|---|---|
| Total Charges | $24,244,799 |
| Total Charge Change Impact | $1,815,911 |
| Allowed to Enforce | $1,815,911 |
| % of Codes Included in Aggregation | 100.00% |

1206 — Contract Information

| | |
|---|---|
| CPL | 0.00% |
| % OP POC | 100.00% |
| Current Contract Effective Date | 10/01/2019 |
| Next Contract Effective Date | 10/01/2019 |

1208 — Detection Details

| | |
|---|---|
| Claimlines | 1,406 |
| Valid Changepoints | 17 |
| Spikes | 14 |
| Units | 10,024 |

1210 — Sub-Categories
Click on a sub-category to view more details at the code level.

1212 —

| Service Category | Allowed to Enforce | CMI % Increase | Total Charge Change Impact | Total Charges Since Last CMI | Units Since Last CMI |
|---|---|---|---|---|---|
| ER Level I | $1,406,892 | 14.02% | $1,406,892 | $19,148,518 | 7,938 |
| ER Level II | $406,319 | 15.84% | $406,319 | $5,036,943 | 1,903 |
| ER Level III | $630 | 2.09% | $630 | $30,744 | 126 |

1214 — CMI % Increase
1216 — Total Charge Change Impact
1218 — 
1220 — Total Charges Since Last CMI
1222 — Units Since Last CMI

*FIG. 12*

Regional Medical Center

ER Level I

Sub-Category Findings
| | |
|---|---|
| Detected CMI % Increase | 14.02% |
| Data Cleanliness | 5/5 |
| Date of Surveillance | 08/01/2020 |
| Detected CMI Date | 10/02/2019 |

Since Last Detected CMI
| | |
|---|---|
| Total Charges | $19,148,518 |
| Total Charge Change Impact | $1,406,892 |
| Allowed to Enforce | $1,406,892 |
| % of Codes Included in Aggregation | 100.00% |

Contract Information
| | |
|---|---|
| CPL | 0.00% |
| % OP POC | 100.00% |
| Current Contract Effective Date | 10/01/2019 |
| Next Contract Effective Date | 10/01/2019 |

Detection Details
| | |
|---|---|
| Claimlines | 608 |
| Valid Changepoints | 2 |
| Spikes | 2 |
| Units | 7,938 |

Service Code
Click on a sub-category to view more details at the code level.

| Service Code | Description | Allowed to Enforce | CMI % Increase | Total Charge Change Impact | Total Charges Since Last CMI | Units Since Last CMI |
|---|---|---|---|---|---|---|
| 99284 | Lorem ipsum... | $997,236 | 7.00% | $997,236 | $1,802,980 | $997,236 |
| 99283 | Lorem ipsum... | $409,656 | 7.02% | $409,656 | $5,345,538 | $409,656 |

*FIG. 13*

| Provider Category Code ID | Provider ID | Category ID | Code ID | Date of Claimline | Charge of Claimline | Unit Count | Billed per Unit (Raw) | Allowed Amount | Billed per Unit (Rounded) | Billed per Unit (Filtered) | Spike Flag |
|---|---|---|---|---|---|---|---|---|---|---|---|
| 0635355-0-1999-370 | 0635355 | 0 | 1999-370 | 2018-08-17 | 1784 | 2 | 892.5 | 665.81 | 892 | 892 | FALSE |
| 0635355-0-1999-370 | 0635355 | 0 | 1999-370 | 2018-12-06 | 2865 | 5 | 573 | 1068.65 | 573 | 573 | FALSE |
| 0635355-0-249T-251 | 0635355 | 0 | 249T-251 | 2018-05-25 | 15.8 | 10 | 1.576 | 5.88 | 1.58 | 1.58 | FALSE |
| 0635355-0-251- | 0635355 | 0 | 251- | 2018-11-27 | 16 | 1 | 15.76 | 5.88 | 16 | 16 | FALSE |
| 0635355-0-370- | 0635355 | 0 | 370- | 2018-11-25 | 2865 | 5 | 573 | 834.38 | 573 | 573 | FALSE |
| 0635355-0-399T-483 | 0635355 | 0 | 399T-483 | 2019-08-27 | 966 | 1 | 966 | 359.35 | 966 | 966 | FALSE |
| 0635355-0-399T-483 | 0635355 | 0 | 399T-483 | 2019-09-23 | 966 | 1 | 966 | 359.35 | 966 | 966 | FALSE |
| 0635355-0-399T-483 | 0635355 | 0 | 399T-483 | 2019-09-24 | 966 | 1 | 966 | 359.35 | 966 | 966 | FALSE |
| 0635355-0-399T-483 | 0635355 | 0 | 399T-483 | 2019-09-30 | 966 | 1 | 966 | 359.35 | 966 | 966 | FALSE |
| 0635355-0-399T-483 | 0635355 | 0 | 399T-483 | 2019-10-01 | 966 | 1 | 966 | 359.35 | 966 | 966 | FALSE |
| 0635355-0-399T-483 | 0635355 | 0 | 399T-483 | 2019-10-14 | 966 | 1 | 966 | 359.35 | 966 | 966 | FALSE |
| 0635355-0-399T-483 | 0635355 | 0 | 399T-483 | 2019-10-15 | 966 | 1 | 966 | 359.35 | 966 | 966 | FALSE |
| 0635355-0-399T-483 | 0635355 | 0 | 399T-483 | 2019-10-23 | 966 | 1 | 966 | 359.35 | 966 | 966 | FALSE |
| 0635355-0-399T-483 | 0635355 | 0 | 399T-483 | 2019-11-14 | 966 | 1 | 966 | 359.35 | 966 | 966 | FALSE |
| 0635355-0-399T-483 | 0635355 | 0 | 399T-483 | 2019-11-27 | 966 | 1 | 966 | 359.35 | 966 | 966 | FALSE |

FIG. 15

| Provider Category Code ID | Provider ID | Category ID | Code ID | Last CMI Date | Data Cleanliness | No. of Claimlines | No. of Changepoints | No. of Spikes | Mode of Unit Charge Before CMI | Mode of Unit Charge after CMI | Percent Increase at CMI | Total Charge | Total Allowed Amount | Unit Count | Charge Change Since CMI |
|---|---|---|---|---|---|---|---|---|---|---|---|---|---|---|---|
| 0635355-0-90837-914 | 0635355 | 0 | 90837-914 | 2020-01-03 | 83.335 | 3 | 1 | 0 | 427 | 468 | 9.60 | 1404 | 1123.2 | 3 | 123 |
| 0635355-0-91065-920 | 0635355 | 0 | 91065-920 | 2020-01-03 | 90 | 5 | 1 | 0 | 900 | 987 | 9.67 | 5922 | 2191.14 | 6 | 522 |
| 0635355-0-92537-471 | 0635355 | 0 | 92537-471 | 2020-01-03 | 0 | 1 | 0 | 0 | 341 | 341 | 0.00 | 341 | 126.17 | 1 | 0 |
| 0635355-0-92540-471 | 0635355 | 0 | 92540-471 | 2020-01-03 | 0 | 1 | 0 | 0 | 1566 | 1566 | 0.00 | 1566 | 579.42 | 1 | 0 |
| 0635355-0-92555-471 | 0635355 | 0 | 92555-471 | 2020-01-03 | 0 | 1 | 0 | 0 | 91 | 91 | 0.00 | 91 | 33.67 | 1 | 0 |
| 0635355-0-92557-471 | 0635355 | 0 | 92557-471 | 2020-01-03 | 100 | 3 | 0 | 0 | 356 | 356 | 0.00 | 1068 | 395.16 | 3 | 0 |
| 0635355-0-92567-471 | 0635355 | 0 | 92567-471 | 2020-01-03 | 100 | 3 | 0 | 0 | 171 | 171 | 0.00 | 513 | 189.81 | 3 | 0 |
| 0635355-0-92570-470 | 0635355 | 0 | 92570-470 | 2020-01-03 | 0 | 1 | 0 | 0 | 509 | 509 | 0.00 | 509 | 188.33 | 1 | 0 |
| 0635355-0-92579-471 | 0635355 | 0 | 92579-471 | 2020-01-03 | 100 | 2 | 0 | 0 | 170 | 170 | 0.00 | 340 | 125.8 | 2 | 0 |
| 0635355-0-92587-471 | 0635355 | 0 | 92587-471 | 2020-01-03 | 0 | 2 | 0 | 0 | 318 | 318 | 0.00 | 636 | 235.32 | 2 | 0 |
| 0635355-0-92588-471 | 0635355 | 0 | 92588-471 | 2020-01-03 | 0 | 1 | 0 | 0 | 513 | 513 | 0.00 | 513 | 189.81 | 1 | 0 |
| 0635355-0-92620-471 | 0635355 | 0 | 92620-471 | 2020-01-03 | 0 | 1 | 0 | 0 | 430 | 430 | 0.00 | 430 | 159.1 | 1 | 0 |
| 0635355-0-96360-260 | 0635355 | 0 | 96360-260 | 2020-01-03 | 78.9 | 10 | 1 | 2 | 357 | 379 | 6.16 | 5716 | 1833.4 | 12 | 1432 |
| 0635355-0-96361-260 | 0635355 | 0 | 96361-260 | 2020-01-03 | 61.615 | 9 | 4 | 1 | 99 | 276 | 178.79 | 4428 | 1529.33 | 21 | 2349 |
| 0635355-0-96365-260 | 0635355 | 0 | 96365-260 | 2020-01-03 | 75.47 | 30 | 3 | 5 | 581 | 616 | 6.02 | 37895 | 13367.15 | 60 | 3035 |

FIG. 16

| Provider Category Code ID | Provider ID | Category ID | Code ID | Date of Claimline | Charge of Claimline | Unit Count | Billed per Unit (Raw) | Allowed Amount | Billed per Unit (Rounded) | Billed per Unit (Filtered) | Spike Flag | Diff. from Baseline | Diff. from Baseline (No Spike) | Change-point Type | Last CMI Date |
|---|---|---|---|---|---|---|---|---|---|---|---|---|---|---|---|
| 0635355-0-96360-260 | 0635355 | 0 | 96360-260 | 2020-02-14 | 671 | 1 | 671 | 200.44 | 671 | 671 | FALSE | 292 | 292 | valid | 2020-01-03 |
| 0635355-0-96365-260 | 0635355 | 0 | 96365-260 | 2020-02-04 | 1342 | 2 | 671 | 474.91 | 671 | 671 | FALSE | 55 | 55 | valid | 2020-01-03 |
| 0635355-0-96365-260 | 0635355 | 0 | 96365-260 | 2020-02-13 | 1848 | 3 | 615.62 | 681.06 | 616 | 616 | FALSE | 0 | 0 | valid | 2020-01-03 |
| 0635355-0-96365-260 | 0635355 | 0 | 96365-260 | 2020-02-18 | 671 | 1 | 671 | 122.03 | 671 | 671 | FALSE | 55 | 55 | valid | 2020-01-03 |
| 0635355-0-96366-260 | 0635355 | 0 | 96366-260 | 2020-02-19 | 828 | 3 | 276 | 306.36 | 276 | 276 | FALSE | 171 | 171 | valid | 2020-01-03 |
| 0635355-0-96374-260 | 0635355 | 0 | 96374-260 | 2020-02-06 | 758 | 2 | 378.65 | 188.99 | 379 | 279 | TRUE | 100 | 0 | spike | 2020-01-03 |
| 0635355-0-96375-260 | 0635355 | 0 | 96375-260 | 2020-02-05 | 942 | 6 | 156.52 | 219.05 | 157 | 279 | TRUE | -122 | 0 | spike | 2020-01-03 |
| 0635355-0-96375-260 | 0635355 | 0 | 96375-260 | 2020-02-07 | 157 | 1 | 156.52 | 57.91 | 157 | 279 | TRUE | -122 | 0 | spike | 2020-01-03 |
| 0635355-0-96375-260 | 0635355 | 0 | 96375-260 | 2020-02-10 | 157 | 1 | 156.52 | 57.91 | 157 | 279 | TRUE | -122 | 0 | spike | 2020-01-03 |
| 0635355-0-96375-260 | 0635355 | 0 | 96375-260 | 2020-02-12 | 157 | 1 | 156.52 | 0 | 157 | 157 | FALSE | -122 | -122 | valid | 2020-01-03 |
| 0635355-0-97802-942 | 0635355 | 0 | 97802-942 | 2020-02-06 | 373 | 1 | 373 | 138.01 | 373 | 373 | FALSE | 302 | 302 | valid | 2020-01-03 |
| 0635355-0-97803-942 | 0635355 | 0 | 97803-942 | 2020-02-03 | 160 | 1 | 160 | 59.2 | 160 | 160 | FALSE | 95 | 95 | valid | 2020-01-03 |
| 0635355-0-A9270-637 | 0635355 | 0 | A9270-637 | 2020-02-05 | 6.57 | 1 | 6.57 | 0 | 6.57 | 3.62 | TRUE | 2.95 | 0 | spike | 2020-01-03 |
| 0635355-0-C1725-272 | 0635355 | 0 | C1725-272 | 2020-02-13 | 1520 | 2 | 759.525 | 562.05 | 760 | 760 | FALSE | 20 | 20 | valid | 2020-01-03 |
| 0635355-0-C1732-272 | 0635355 | 0 | C1732-272 | 2020-02-03 | 53859 | 3 | 17953.2 | 19784.25 | 17953 | 17953 | FALSE | 1497 | 1497 | valid | 2020-01-03 |

FIG. 17

| Provider ID | Surveillance Date | Alert Type | CMI Date | Data Cleanliness | No. of Claimlines | No. of Change-points | No. of Spikes | Unit Count | Total Charge | Charge Change Since CMI | Provider CMI Percent Increase |
|---|---|---|---|---|---|---|---|---|---|---|---|
| 0635355 | 2020-03-01 | MONTHLY INCREASE ALERT | 2020-01-03 | 85.73485413 | 8844 | 625 | 320 | 112453 | 41953282 | 5117413 | 284.7157 |
| 4477823 | 2020-03-01 | MONTHLY INCREASE ALERT | 2019-10-02 | 94.21865599 | 21782 | 513 | 325 | 98652 | 64570159 | 4169618 | 5.803443 |
| 0186606 | 2020-03-01 | MONTHLY INCREASE ALERT | 2020-01-16 | 92.51932432 | 3824 | 137 | 66 | 18173 | 4095303 | 325346.4 | 8.865205 |
| 0451626 | 2020-03-01 | MONTHLY INCREASE ALERT | 2020-01-16 | 86.24278772 | 3257 | 287 | 168 | 8516 | 2304341 | 218281.2 | 16.12442 |

FIG. 18

| Billing Code | CMI Percent Increase | Total Charges Since Last CMI | Total Charge Change Impact | Amount Allowed To Enforce | Units Since Last CMI | Valid Changepoints Since Last CMI | Data Cleanliness | Weighted CMI by Charges |
|---|---|---|---|---|---|---|---|---|
| 47562-360 | -1.77 | $237,686 | $82,414 | $73,874 | 13 | 5 | 2 | -0.951436345 |
| 47563-360 | 408.64 | $150,744 | $91,024 | $87,739 | 5 | 0 | 0 | 139.3104771 |
| 74177-350 | 9.7 | $12,201 | $1,079 | $467 | 1 | 1 | 0 | 0.267651715 |
| 88304-312 | 9.73 | $11,160 | $990 | $431 | 18 | 1 | 5 | 0.245572597 |
| G0378-762 | 9.79 | $7,998 | $713 | $312 | 31 | 1 | 4 | 0.177078959 |
| 99285-450 | 11.97 | $7,877 | $842 | $455 | 1 | 0 | 0 | 0.213234693 |
| 74300-320 | 9.66 | $5,620 | $495 | $213 | 5 | 1 | 4 | 0.1227768 |
| J3490-636 | -82.27 | $4,702 | ($253,774.00) | ($267,990.18) | 716 | 2 | 4 | -0.874836695 |
| 88313-312 | 9.69 | $4,190 | $370 | $160 | 10 | 1 | 4 | 0.091820715 |
| Sum of Total Charges Since Last CMI | | $442,178 | | | | | CMI at Category Level: | 138.6023396 |

FIG. 19

COMPUTERIZED TIME-SERIES ANALYSIS FOR INFERENCE OF CORRELATED INPUT MODIFICATIONS

CROSS-REFERENCE TO RELATED APPLICATIONS

This application is a continuation of U.S. patent application Ser. No. 17/123,855 filed Dec. 16, 2020, the entire disclosure of which is incorporated by reference.

FIELD

The present disclosure relates to computerized big data analysis and more particularly to computerized inference of changes to a set of inputs occurring at a certain point in time.

BACKGROUND

The chargemaster is the healthcare provider's internal book of items billable to a patient or insurance provider. The chargemaster includes a listing of fees, for example, for services, procedures, drugs, medical supplies, tests, equipment, etc. Each item in the chargemaster is assigned a unique billing code (sometimes referred to as a revenue code, a service code, a procedure code, a current procedural terminology ("CPT") code, a modifier code, simply a code, and/or any combination of the foregoing) and an associated price or charge for that code. Therefore, the claim or invoice for each item or code is based on the provider's chargemaster. Insurance companies will attempt to enter into fixed-rate contracts for each code. However, in reality, entering into fixed-rate contracts with providers is not always possible for insurance companies. Therefore, insurance companies will agree to pay the provider's chargemaster rate or a discount off of the rate (e.g., a 10% discount). In the case of a fixed-rate contract, the provider may bill $15,000 for the code for a hip surgery, if the contract states that insurance will only reimburse $10,000 then the insurer will pay the contracted rate. However, if the contract states that the insurer will pay a discount off of the rate, the insurer will be exposed to rate increases determined by the provider. The provider is allowed to raise their chargemaster rates at any time, often without notice to the insurer. Thus, an insurer would benefit with additional information regarding a provider's chargemaster.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized analysis system includes a data retrieval module configured to retrieve claimline data for a period of time from an input data store. The claimline data includes billing codes and prices of the billing codes associated with a provider. An analysis module is configured to receive the claimline data from the data retrieval module, determine whether a changepoint exists in the billing codes in the claimline data, determine a statistical parameter of changepoints per day during the period of time, and identify a chargemaster increase for the provider in response to the statistical parameter of changepoints exceeding a threshold.

An alert module is configured to, in response to identification of a chargemaster increase, publish an alert that a chargemaster increase has occurred for the provider. The alert includes at least one of an identification of the provider, a chargemaster increase date, a number of claimlines, a number of changepoints, an identification of the billing code, and a price of the billing code at the changepoint. The alert is configured to transform a user interface displayed to a user.

In other features, the system includes a web server configured to create the user interface for display to the user and transform the user interface in response to the alert. In other features, the analysis module is configured to aggregate same-day prices of the billing codes to create a single time series for each billing code, obtain historical changepoint data from an output data store, obtain historical claimline data since a last chargemaster increase, and determine a baseline price for each billing code. In other features, the system includes a spike filter module configured to flag and filter spikes in the prices of the billing codes in the claimline data. The analysis module is configured to, in response to determining that a changepoint exists, classify the changepoint as one of a spike, a repeat, and a valid changepoint. In other features, the system includes a scheduler module configured to control execution of the analysis module.

In other features, the scheduler module is configured to, in response to a determination that a periodic interval has occurred, set a lookback period for the analysis module to process and instruct the analysis module to analyze claimline data of the earliest time period in the lookback period and sequentially analyze claimline data of subsequent time periods in the lookback period until the claimline data of all time periods of the lookback period are analyzed. The lookback period includes a number of past time periods. In other features, the system includes a listener module configured to enforce a chargemaster cap.

In other features, the listener module is configured to, in response to publication of an alert, extract a discount corresponding to the billing code from a contract with the provider, where the contract is stored in the input data store, extract a cap corresponding to the billing code from the contract, calculate a percent increase of the price at the changepoint compared to a baseline price for the billing code, in response to a determination that the percent increase of the price at the changepoint is greater than the cap, calculate an adjusted discount for the billing code, and create a new contract having the adjusted discount. In other features, the system includes an output data store configured to store at least one of changepoint data, alert data, filtered claimline data, and multi-level metric data.

A computerized method of identifying a chargemaster increase includes retrieving claimline data for a period of time from an input data store. The claimline data includes billing codes and prices of the billing codes associated with a provider. The method further includes determining whether a changepoint exists in the billing codes in the claimline data, determining a statistical parameter of changepoints per day during the period of time, and identifying a chargemaster increase for the provider in response to the statistical parameter of changepoints exceeding a threshold. The method includes, in response to identification of a chargemaster increase, publishing an alert that a chargemaster increase has occurred for the provider. The alert includes at least one of an identification of the provider, a chargemaster increase date, a number of claimlines, a number of changepoints, an identification of the billing code, and a price of the billing code at the changepoint. The method further includes creating a user interface for display to a user. The user interface includes the alert.

In other features, the method includes aggregating same-day prices of the billing codes to create a single time series for each billing code, obtaining historical changepoint data from an output data store, obtaining historical claimline data since a last chargemaster increase, and determining a baseline price for each billing code. In other features, the method includes in response to determining that a changepoint exists, classifying the changepoint as one of a spike, a repeat, and a valid changepoint. In other features, the method includes in response to determining that a changepoint exists, appending the changepoint to an output data store.

In other features, the method includes, in response to publication of the alert, extracting a discount corresponding to the billing code from a contract with the provider, where the contract is stored in the input data store. The method further includes extracting a cap corresponding to the billing code from the contract and calculating a percent increase of the price at the changepoint compared to a baseline price for the billing code. The method further includes, in response to a determination that the percent increase of the price at the changepoint is greater than the cap, calculating an adjusted discount for the billing code. The method further includes creating a new contract with the provider having the adjusted discount.

A non-transitory computer-readable medium stores processor-executable instructions. The instructions include (i) identifying that a periodic interval has occurred, and (ii) setting a lookback period. The lookback period includes a number M of past months. The instructions further include (iii) selecting the month that is M months before the current month, (iv) obtaining claimline data of a provider from an input data store, (v) identifying a billing code in the claimline data for the selected month, (vi) creating a single time series of prices for the billing code by aggregating same-day billing code prices in the claimline data for the selected month, and (vii) determining a baseline price for the billing code. The instructions further include (viii) comparing a price for the billing code in the single time series to the baseline price to determine a changepoint, (ix) counting the number of changepoints for each day of the selected month, (x) determining a statistical parameter of changepoints per day throughout the selected month, and (xi) determining whether a maximum number of changepoints on any given day exceeds the statistical parameter of changepoints per day by a threshold. The instructions further include (xii) in response to determining that the maximum number of changepoints exceeds the statistical parameter of changepoints per day by the threshold, selecting the day of the month with the maximum number of changepoints. The instructions further include (xiii) identifying a chargemaster increase for the selected day and (xiv) in response to identifying a chargemaster increase, generating an alert for display to a user in a user interface that indicates that the chargemaster increase has occurred for the provider.

In other features, the instructions include decrementing M by one, determining whether M is equal to 0, and in response to determining that M is not equal to 0, repeating steps (iii)—(xiv). In other features, the instructions include filtering and flagging a set of spikes in the time series of prices for the billing code and classifying a changepoint as one of a spike, a repeat, and a valid changepoint. In other features, $M=3$.

In other features, the instructions include, in response to generation of an alert, extracting a discount corresponding to the billing code from a contract with the provider, where the contract is stored in the input data store, extracting a cap corresponding to the billing code from the contract, and calculating a percent increase of the price at the changepoint of the billing code compared to the baseline price for the billing code. The instructions further include, in response to a determination that the percent increase of the price at the changepoint is greater than the cap, calculating an adjusted discount for the billing code. The instructions further include creating a new contract having the adjusted discount. In other features, the instructions include generating an alert for display to a user in a user interface that indicates that the new contract has been created for the provider.

A computerized analysis system includes a data retrieval module, a spike filter module, a chargemaster analysis module, and an alert module. The data retrieval module is configured to retrieve claimline data for a period of time from an input data store. The claimline data includes billing codes and prices of the billing codes associated with a provider. The spike filter module is configured to flag and filter price spikes in the claimline data. The chargemaster analysis module is configured to determine whether a changepoint exists in the billing codes in the claimline data. The chargemaster analysis module is configured to identify a chargemaster increase for the provider in response to a statistical parameter of changepoints exceeding a threshold. The alert module is configured to, in response to identification of a chargemaster increase, publish an alert that a chargemaster increase has occurred for the provider.

In other features, the system includes a web server configured to create a user interface for display to a user based on the alert. In other features, the spike filter module is configured to set $n=1$, create a time series of billing codes from the claimline data, and select a data point of the time series. The selected data point is not the second to last data point of the time series. The spike filter module is further configured to flag the selected data point as a spike in response to a determination that the selected data point is not equal to any of an n earlier data point of the time series, an n later data point of the time series, an n+1 earlier data point of the time series, and an n+1 later data point of the time series. The spike filter module is further configured to copy the selected data point to a filtered claimline data in response to a determination that the selected data point is equal to any one of the n earlier data point of the time series, the n later data point of the time series, the n+1 earlier data point of the time series, and the n+1 later data point of the time series.

In other features, the time series includes the last two data points of an initial time series of billing codes from the claimline data from a period of time immediately prior to the period of time and the data points of an initial time series of billing codes from the claimline data for the period of time. In other features, the spike filter module is configured to classify the last data point in the initial time series of billing codes from the claimline data from the prior period of time in response to a determination that the last data point is not equal to the second to last data point in the initial time series of billing codes from the claimline data from the prior period of time, and the first data point in the initial time series of billing codes from the claimline data for the period of time.

In other features, the spike filter module is configured to set $n=1$, create a time series of billing codes from the claimline data, and select a data point of the time series. The selected data point is the second to last data point of the time series for the period of time. The spike filter module is further configured to flag the selected data point as a spike in response to a determination that the selected data point is not equal to any of an n earlier data point of the time series, an n later data point of the time series, and an n+1 earlier data point of the time series. The spike filter module is further configured to copy the selected data point to a filtered claimline data in response to a determination that the selected data point is equal to any one of the n earlier data point of the time series, the n later data point of the time series, and the n+1 earlier data point of the time series.

In other features, the time series includes the last two data points of an initial time series of billing codes from the claimline data for a period of time immediately prior to the period of time and the data points of an initial time series of billing codes of the claimline data for the period of time. In other features, the spike filter module is configured to classify the last data point in the initial time series of billing codes from the claimline data from the prior period of time in response to a determination that the last data point is not equal to the second to last data point in the initial time series of billing codes from the claimline data from the prior period of time and the first data point in the initial time series of billing codes from the claimline data for the period of time.

In other features, the chargemaster analysis module is configured to obtain historical changepoint data from an output data store, obtain historical claimline data since a last chargemaster increase, and determine a baseline price for each billing code. In other features, the alert includes at least one of an identification of the provider, a chargemaster increase date, a number of claimlines, a number of changepoints, an identification of the billing code, and a price of the billing code at the changepoint. In other features, the system includes a listener module configured to enforce a chargemaster cap.

In other features, the listener module is configured to, in response to publication of an alert extract a discount corresponding to the billing code from a contract with the provider, where the contract is stored in the input data store. The listener module is further configured to extract a cap corresponding to the billing code from the contract and calculate a percent increase of the price of the billing code at the changepoint compared to a baseline price for the billing code. The listener module is further configured to, in response to a determination that the percent increase of the price of the billing code at the changepoint is greater than the cap, calculate an adjusted discount for the billing code. The listener module is further configured to create a new contract having the adjusted discount.

A computerized method of identifying a chargemaster increase includes retrieving claimline data for a period of time from an input data store, the claimline data includes a billing codes and prices of the billing codes associated with a provider. The method further includes creating a time series of billing codes from the claimline data and selecting a data point of the time series. The selected data point is not the second to last data point of the time series. The method further includes flagging the selected data point as a spike in response to a determination that the selected data point is not equal to one or more preceding data points of the time series or one or more subsequent data points of the time series. The method further includes copying the selected data point to a filtered claimline data in response to a determination that the selected data point is equal to one or more preceding data points of the time series or one or more subsequent data points of the time series. The method further includes determining whether a changepoint exists in the billing codes in the claimline data. The method further includes in response to determining that a changepoint exists, classifying the changepoint. The method further includes identifying a chargemaster increase for the provider in response to a statistical parameter of changepoints exceeding a threshold and, in response to identification of a chargemaster increase, publishing an alert that a chargemaster increase has occurred for the provider. The method further includes creating a user interface for display to a user. The user interface includes the alert.

In other features, the method includes classifying the last data point in an initial time series of billing codes from the claimline data for a period of time immediately prior to the period of time in response to a determination that the last data point is not equal to the second to last data point in the initial time series of billing codes from the claimline data from the prior period of time and the first data point in an initial time series of billing codes from the claimline data for the period of time.

In other features, the method includes obtaining historical changepoint data from an output data store, obtaining historical claimline data since a last chargemaster increase, and determining a baseline price for each billing code. In other features, the method includes, in response to determining that a changepoint exists, classifying the changepoint as one of a spike, a repeat, and a valid changepoint. In other features, the method includes, in response to determining that a changepoint exists, appending the changepoint to an output data store.

In other features, the method includes, in response to publication of the alert extracting a discount corresponding to the billing code from a contract with the provider, where the contract is stored in the input data store, extracting a cap corresponding to the billing code from the contract, and calculating a percent increase of the price of the billing code at the changepoint compared to a baseline price for the billing code. The method further includes, in response to a determination that the percent increase of the price of the billing code at the changepoint is greater than the cap, calculating an adjusted discount for the billing code. The method further includes creating a new contract with the provider having the adjusted discount.

A non-transitory computer-readable medium stores processor-executable instructions. The instructions include obtaining claimline data of a provider from an input data store, identifying a billing code in the claimline data for a selected month, and creating a time series of prices for the billing code by aggregating same-day billing code prices in the claimline data for the selected month. The instructions further include selecting a data point of the time series for the selected month and flagging the selected data point as a spike in response to a determination that the selected data point is not equal to one or more preceding data points of the time series or one or more subsequent data points of the time series. The instructions further include copying the selected data point to a filtered claimline data in response to a determination that the selected data point is equal to one or more preceding data points of the time series or one or more subsequent data points of the time series. The instructions further include, in response to one or more of flagging the selected data point as a spike, generating an indicia for display to a user in a user interface that indicates that the price of the billing code of the selected data point is a spike.

In other features, the instructions include determining a baseline price for the billing code and comparing a price for the billing code in the time series to the baseline price to determine a changepoint. The instructions further include, for each day of the selected month, counting a total number of changepoints. The instructions further include determining a statistical parameter of changepoints per day throughout the selected month and determining whether a maximum number of changepoints on any given day exceeds the statistical parameter of changepoints per day by a threshold. The instructions further include, in response to determining that the maximum number of changepoints exceeds the statistical parameter of changepoints per day by the threshold, selecting the day of the month with the maximum number of changepoints. The instructions further include identifying a chargemaster increase for the selected day.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 11-14 are example user interfaces that may be presented by a user device to an operator according to the principles of the present disclosure.

FIGS. 15-18 are example data tables showing data from an output data store according to the principles of the present disclosure.

FIG. 19 is a table showing example data from an output data store according to the principles of the present disclosure.

In the drawings, reference numbers may be reused to identify similar and/or identical elements.

DETAILED DESCRIPTION

Described herein are systems, methods and apparatuses configured to determine chargemaster rates for providers and to identify when a chargemaster increase ("CMI") has occurred. This impacts the ability of insurers to control costs and determine where to send patients.

Figure 1:
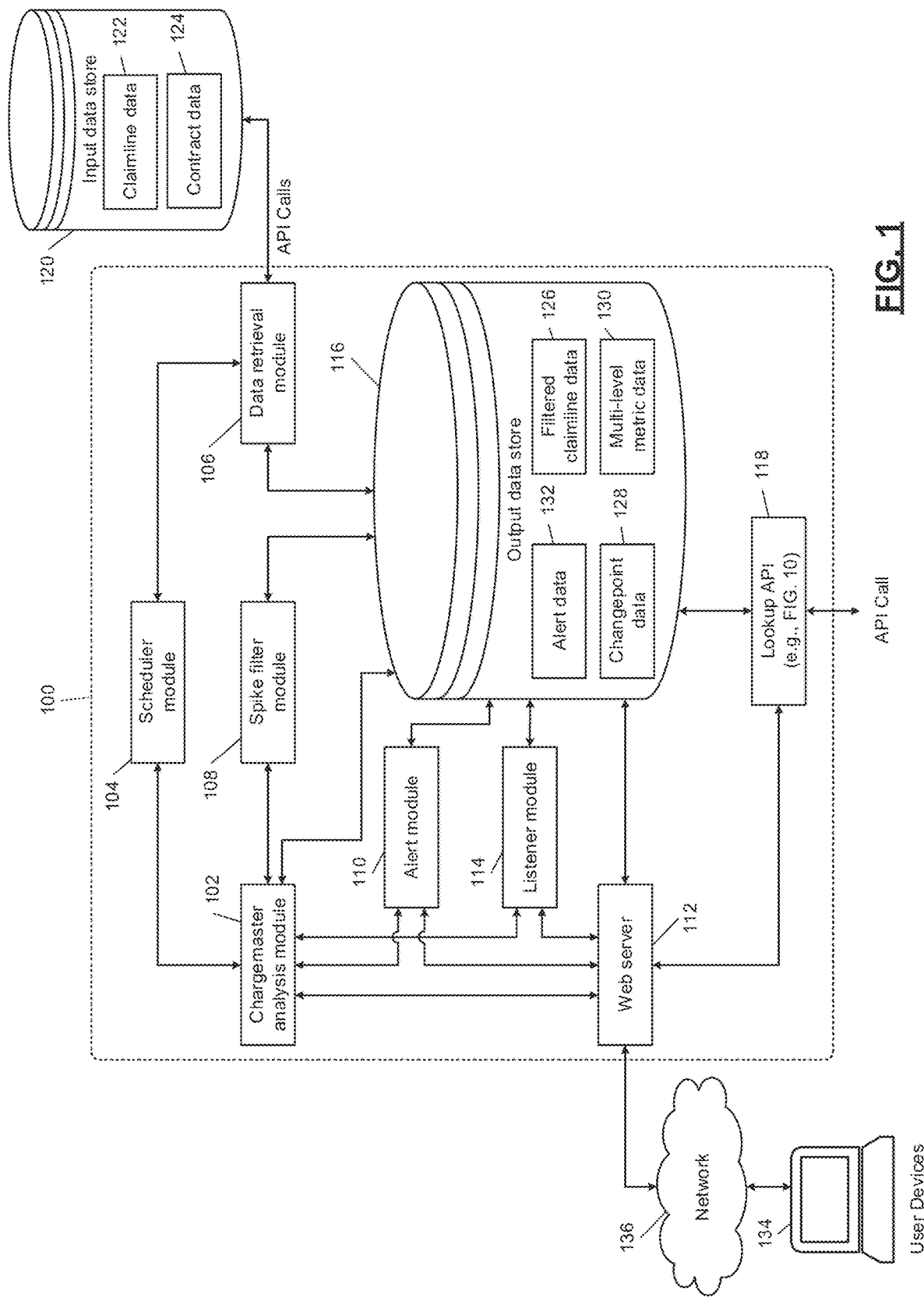
FIG. 1 is a functional block diagram of an example implementation of a chargemaster analysis system according to the principles of the present disclosure.

FIG. 1 is a functional block diagram of an example implementation of a chargemaster analysis system 100. The chargemaster analysis system 100 includes a chargemaster analysis module 102, a scheduler module 104, a data retrieval module 106, a spike filter module 108, an alert module 110, a web server 112, a listener module 114, an output data store 116, and a lookup API 118. The chargemaster analysis system 100 is configured to determine changes in prices (or changepoints) for billing codes from providers and to identify when a chargemaster increase has occurred.

The chargemaster analysis module 102 may be triggered to run on a periodic basis, such as for example, once a month. The scheduler module 104 controls when the chargemaster analysis module 102 executes. In response to a determination that a periodic interval has occurred, the scheduler module 104 is configured to set a lookback period for the chargemaster analysis module 102 to process. The lookback period may be a number of past time periods for the chargemaster analysis module 102 to process.

In some embodiments, the scheduler module 104 instructs the chargemaster analysis module 102 to analyze claimline data of the earliest time period in the lookback period and sequentially analyze claimline data of subsequent time periods in the lookback period until claimline data of all time periods of the lookback period are analyzed. The scheduler module 104 allows the chargemaster analysis system 100 to operate at large scale (see, for example, FIG. 11).

The data retrieval module 106 is configured to access an input data store 120 in order to retrieve raw claimline data 122 and contract data 124 stored on the input data store 120 corresponding to one or more providers. The raw claimline data 122 includes a provider ID, a billing code, a price for the billing code, and a date on which the billing code was performed or rendered. In some embodiments, the data retrieval module 106 may access the input data store 120 via an API call. In some embodiments, the data retrieval module 106 creates a copy of the raw claimline data 122 and the contract data 124 for analysis by the chargemaster analysis module 102. The copy of the claimline data 122 and the contract data 124 may be at least temporarily stored in the output data store 116.

In some embodiments, the data retrieval module 106 accesses the raw claimline data 122 and the contract data 124 from the input data store 120 in real time during analysis by the chargemaster analysis module 102. The input data store 120 and the output data store 116 may be located in separate servers or within the same server. In some embodiments, the input data store 120 and the output data store 116 may be separate databases. In some embodiments, the input data store 120 and the output data store 116 are in a single database.

The spike filter module 108 is configured to flag and filter price spikes in the claimline data 122 and can store filtered claimline data 126 in the output data store 116. The chargemaster analysis module 102 may receive the filtered claimline data 126 from the output data store 116 during analysis.

The chargemaster analysis module 102 is also configured to generate changepoint data 128 and multi-level metric data 130. The multi-level metric data 130 may include one or more of code-level metric data, sub-category-level metric data, category-level metric data, and provider-level metric data. The changepoint data 128 and multi-level metric data 130 are stored in the output data sore 116. The changepoint data 128 and multi-level metric data 130 may be retrieved from the output data store 116 and may be used during successive analyses of new claimline data 122 by the chargemaster analysis module 102. Depending on the output of the analysis performed by the chargemaster analysis module 102, the alert module 110 is configured to build and publish an alert, which may be stored as alert data 132 in the output data store 116. In some embodiments, the alert data 132 may be sent out to other applications and/or services that subscribe to the alerts. The lookup API 118 may be configured to retrieve changepoint data 128 from the output data store 116 and serve it to a consumer via an API call.

An operator may use a user device 134 to access the chargemaster analysis system 100 via a network 136 and the web server 112. The user device 134 may be a desktop computer, kiosk, or mobile computing device, such as a phone or tablet. The user device 134 includes a display screen, which displays one or more user interfaces to an operator. The web server 112 presents a user interface (UI) to the operator. The operator is able to input and receive information from the output data store 116 via the user interface generated by web server 112. The web server 112 transforms the UI in response to alerts. For example, a graphic indicating that an alert has been generated may be displayed prominently to the operator.

Examples of the network 136 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 136 may include an optical network. The network 136 may be a local area network or a global communication network, such as the Internet. Moreover, although the system shows a single network 136, multiple networks can be used. The multiple networks may communicate in series and/or parallel with each other to link the user device 134 and the chargemaster analysis system 100.

Figure 2:
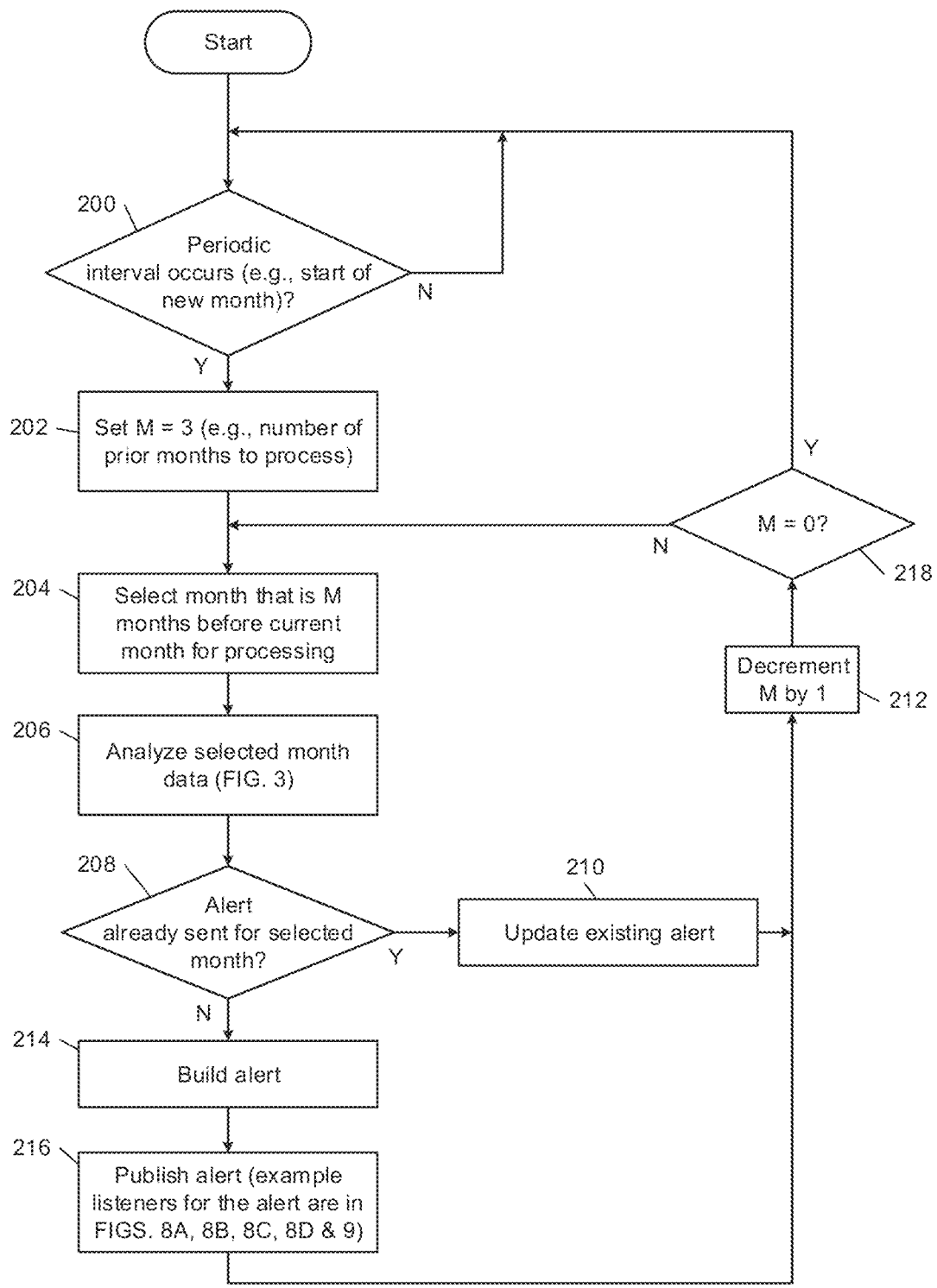
FIG. 2 is a flowchart of an example of an overall surveillance analysis for surveillance of claimline data, identifying a chargemaster increase, and alerting a provider of the increase according to the principles of the present disclosure.

FIG. 2 is a flowchart of an example of an overall surveillance analysis for surveillance of claimline data, identifying a chargemaster increase, and alerting a provider of the increase. The chargemaster analysis system 100 looks back at historical data to identify chargemaster changes. Control begins at 200 where control determines whether a periodic interval has occurred. For example, the periodic interval may be the start of a new month. If so, control transfers to 202; otherwise, control returns to 200. At 202, control sets the lookback period for processing. For example, the lookback period may be a number of past time periods (e.g., months) to process (M).

As shown in FIG. 2, in some embodiments, the number of past time periods to process is set to three months (M=3). In some embodiments, the number of past time periods may be greater than three months (e.g., 4 months, 5 months, 6 months, 9 months, 12 months). For example, in some embodiments, if control encounters a new provider ID for which historical information does not exist in the output data store 116, then control may automatically kick off a full run of claimline data for the provider with M=12 to build up the historical changepoint information for this provider so that it can then be run month-over-month with good results. In some embodiments, the number of past months may be less than three months (e.g., 2 months, 1 month). Although the time period is generally referred to herein as a month, the time period may be measured in days, weeks, or years in various implementations. Additionally, in some embodiments, the lookback period may be a number of days, weeks, or years.

In some embodiments, new claimline data become available from providers on a monthly basis; however, claimline data can lag from providers. That is, a billing code may be rendered in a particular month, but may not appear in the claimline data until one or more subsequent months. This is known as claim run-out. The surveillance analysis includes this lookback period to capture claimline data for prior months and increases the accuracy of the analysis. Thus, during each run of the surveillance analysis, data from a number of prior months equal to the lookback period will be analyzed, starting with the earliest month in the lookback period. In some embodiments, claimline data may become available in real-time.

At 204, control selects the month that is M months before the current month for processing of claimline data 122. At 206, control analyzes the claimline data 122 for the selected month as described in further detail with respect to FIG. 3. At 208, control determines whether an alert has already been sent for the selected month for the selected chargemaster rate. In some embodiments, only one alert is published per provider. For example, if an alert was sent for prior month, as of this month, the contents of that alert may be modified as necessary, such as because another CMI may have occurred). If an alert has already been sent for the selected month, control updates the existing alert at 210 (e.g., to indicate the CMI) and proceeds to 212. Control can save the updated alert in the alert data 132 in the output data store 116. If no alert has been sent, control proceeds to 214. At 214, control builds an alert, and at 216, control publishes the alert.

The alert indicates that a chargemaster increase has occurred for the provider. As described in further detail below, the alert may include, but is not limited to, one or more of a provider ID, a hospital system ID, a regional ID, a surveillance date, a chargemaster increase date, a data cleanliness value, a number of claimlines, a number of changepoints, a price at the changepoint, a number of spikes, a unit count, a total charge, a charge change since the chargemaster increase, and a provider chargemaster increase on a percentage basis. In some embodiments, the alert may be published in a variety of ways, including but not limited to an email, a text message, an SMS, and/or a push notification. The alert can be displayed to an operator in a user interface on the user device 134. The user interface may be created by the web server 112. In some embodiments, in a default view, the user interface may only show alerts where the CMI is greater than a certain percentage and the user may be able to toggle or change what is displayed on the user interface to show additional data in the alert. In some embodiments, the user interface displays an alert when the CMI violates a contract cap. As described in further detail below, one or more listeners may listen for the alert and may conduct further analysis in response to the publication of an alert.

After the alert is published at 216, control proceeds to 212. At 212, control decrements M by 1. At 218, control determines whether M is equal to 0. If so, control returns to 200; otherwise, control returns to 204 to process data from one month after the earliest month in the lookback period. Control loops through 204 and 218 until all months in the lookback period are processed. For example, if the lookback period is three months (M=3) and the current date is July 1, control will first analyze data between April 1 and April 30 (M=3), control will then analyze data between May 1 and May 31 (M=2), and control will then analyze data between June 1 and June 30 (M=1). In this example, when data between June 1 and June 30 is analyzed, there may not be much data. However, when the current date is August 1, and the surveillance is conducted with a three (3) month lookback again, the period between June 1 and June 30 will have more claimline data. The period between June 1 and June 30 may have even more data when the surveillance is conducted again on September 1.

Figure 3:
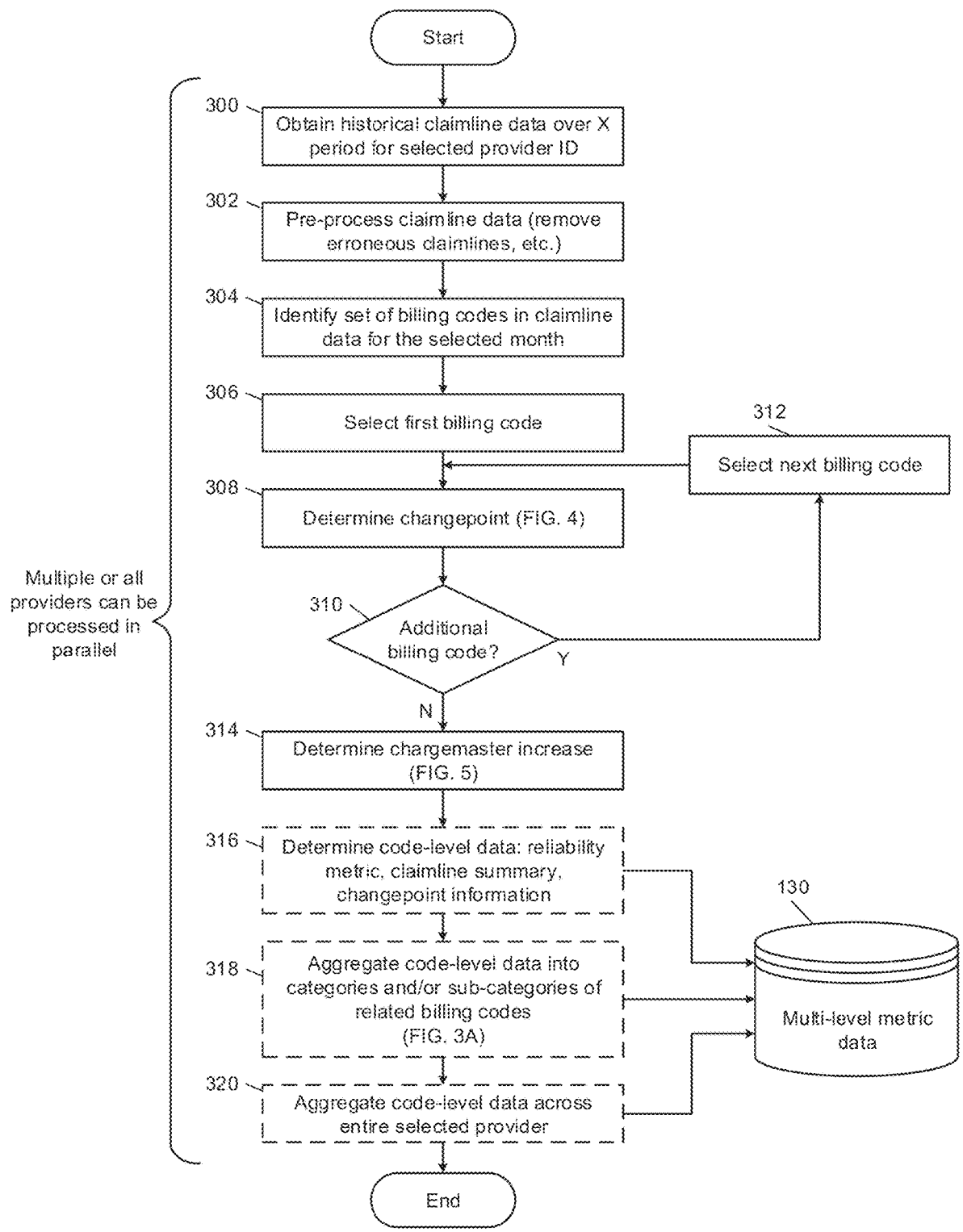
FIG. 3 is a flowchart of an example of an analysis for identifying a chargemaster increase based on claimline data according to the principles of the present disclosure.

FIG. 3 is a flowchart of an example of an analysis for identifying a chargemaster increase based on claimline data. At 300, control then obtains historical claimline data 122 over an X time period for the selected provider ID. Each provider that the insurer has a contract with has a unique provider identification code (ID). In some embodiments, the X time period may be the last year of claimline data 122 for the selected provider ID. In some embodiments, the X time period may be the last two years of claimline data 122 for the selected provider ID. In some embodiments, the X time period may be more than the last two years of claimline data 122 for the selected provider ID. In some embodiments, the X time period may be the last 3 months, 6 months, 9 months, 12 months, 15 months, 18 months, or 24 months of claimline data 122 for the selected provider ID. In some embodiments, a sufficient amount of historical claimline data is obtained to produce relevant metrics for the current month.

At 302, control pre-processes the claimline data 122. Pre-processing the data may include removing erroneous claimlines and creating calculated fields. In some embodiments, pre-processing the data may include discarding small claims (e.g., claims at $1). In some embodiments, pre-processing the data may include accounting for claim adjustments and/or reversals.

At 304, control identifies a set of billing codes in the claimline data 122 for the selected month. At 306, control selects the first billing code from the set of billing codes. At 308, control determines whether there is a changepoint, as described further in FIG. 4. At 310, control determines whether there is an additional billing code to evaluate. If there is an additional billing code to evaluate, at 312 control selects the next billing code and returns to 308. If there is not an additional billing code to evaluate, control proceeds to 314. At 314, control determines whether there is a chargemaster increase, as described further in FIG. 5.

At 316, control can optionally determine various billing code-level data, such as for example, reliability metrics, claimline summaries, changepoint information, the dollar value impact of a chargemaster increase, and the chargemaster increase percent. In some embodiments, the various code-level data are calculated using the data that are used and generated from the current run of the analysis and from prior runs of the analysis. These data may include raw claimline data, the changepoints detected in the current month at 308, historical changepoints detected in previous months from prior runs of the analysis and stored in the changepoint data 128, and the last detected chargemaster increase date.

The reliability metrics are a determination of the consistency of the charges for a specific billing code before and after the detected CMI date. For example, the metric can be an integer from, and inclusive of, zero (0) to five (5), where zero (0) represents the lowest reliability and five (5) represents the highest reliability. In some embodiments, the reliability metric may be calculated as follows. If there is one claimline before or after the CMI date or more than a threshold amount (e.g., one-fourth, one-half, or two-thirds) of the claimlines include unique prices for a billing code, then control sets the reliability metric to zero (0). If there is only one claimline on either side of the CMI date, there may be insufficient information to determine what the baseline price for a billing code should be or what the price of the billing code is presently.

If more than a threshold amount of the claimlines include unique prices for a billing code, this is an indication that there is a high level of fluctuation in the prices and control may be unable to accurately determine other metrics. In some embodiments, billing codes with a reliability metric of zero (0) are not included in the aggregation to the service category-level or the provider category-level at 318 and 320, respectively.

In some embodiments, control can calculate "data cleanliness before the CMI" and "data cleanliness after the CMI." Control may then average the data cleanliness values. The data cleanliness calculation is based on the claimline data before and after the CMI date, the number of spikes, the number of changepoints, and the number of claimlines. The data cleanliness ("DC") can be calculated using Eq. 1 as follows:

$$DC = \left(1 - \left(\frac{\text{Number of spikes} + \text{Number of changepoints}}{\text{Number of claimlines}}\right)\right) \times 100 \quad \text{Eq. 1}$$

Equation 1 results in a number between zero (0) and 100. To calculate the data cleanliness before the CMI, the Number of spikes is the total number of spikes occurring in the claimline data for the current month prior to the CMI date, the Number of changepoints is the total number of changepoints occurring in the claimline data for the current month prior to the CMI, and the Number of claimlines is the total number of claimlines occurring in the claimline data for the current month prior to the CMI. To calculate the data cleanliness after the CMI date, the Number of spikes is the total number of spikes occurring in the claimline data for the current month after the CMI, the Number of changepoints is the total number of changepoints occurring in the claimline data for the current month after the CMI, and the Number of claimlines is the total number of claimlines occurring in the claimline data for the current month after the CMI. Control then averages the data cleanliness before the CMI and the data cleanliness after the CMI, and may round to the nearest integer to calculate a data cleanliness value between zero (0) and 100. In some embodiments, control may divide the average by 20 and may round to the nearest integer to calculate a data cleanliness value between zero (0) and five (5).

In some embodiments, a CMI increase or decrease percentage may also be calculated at 316. For example, control may determine the maximum mode of the prices of a billing code before and after a CMI using filtered claimline data. Control may then determine the percent change in the price of the billing code using the maximum mode of the prices of a billing code before and after a CMI. In some embodiments, control may be able to determine a charge change impact metric that computes the change in charges resulting from a CMI. The charge change impact metric may be a measure of how much more or less an insurer will pay due to the change in the price of the billing code compared to what the insurer would have paid had the insurer continued to pay the same rate (e.g., discount) from prior to the CMI. This may be calculated per claimline by subtracting a baseline price of the billing code from the price of the billing code at the CMI and multiplying that difference by the number of times that particular billing code was charged. One or more of the data determined at 316 may be stored by control in the multi-level metric data 130.

A 318, control can optionally aggregate the billing code-level data into categories and/or sub-categories of related billing codes. For example, each billing code may be classified into a particular service category, such as for example, Surgery, Emergency Room, Diagnostic, Drugs, Durable Medical Equipment ("DME"), etc. Control can aggregate the data for all billing codes in a particular service category and/or sub-category. This may be considered category CMI roll up data. At 320, control can optionally aggregate the billing code-level data across the entire selected provider. For example, each billing code may be classified into a particular provider category, such as for example, inpatient and outpatient. Control can aggregate the data for all billing codes in a particular provider category. This may be considered provider CMI roll up data. One or more of the category CMI roll up data and the provider CMI roll up data determined at 318 and 320, respectively, may be stored by control in the multi-level metric data 130.

At 302 through 314, control analyzes the current month of data to determine changepoints, while at 316 through 320, control produces metrics since the last CMI date and is using data since the last CMI date, which may be a year of data. In some embodiments multiple billing codes and/or providers can be processed in batches or in parallel.

FIG. 19 is an example data table showing data from the output data store 116. In particular, FIG. 19 is an example of the category CMI roll up data shown as a category CMI roll up data table 322. In some embodiments, the category CMI roll up data table 322 may be presented in a user interface by the user device 134 to an operator. Control can take the code-level metrics for any particular category (and/or sub-category) and can compute the same metrics for the category (and/or sub-category) overall by performing one or more operations on the code-level metrics, such as for example, summing, averaging, and/or computing the mode of the code-level metrics.

The category CMI roll up data table 322 may include various data on one or more billing codes within a category and/or sub-category. Each row represents a different billing code. Each column displays an attribute of the billing code. The category CMI roll up data table 322 may include a billing code ID 324, a CMI percent increase 326, a total charge since the last CMI 328, a total charge change impact 330, an amount allowed to enforce 332, a number of units since the last CMI 334, a number of valid changepoints since the last CMI 336, a data cleanliness value 338, and a weighted CMI by charges 340 for the displayed one or more billing codes. The category CMI roll up data table 322 may also include a sum 342 of the total charges since the last CMI 328 and a sum 344 of the weighted CMI by charges 340.

The amount allowed to enforce 322 is the amount more that an insurer paid due to the CMI than previously paid before the CMI minus the amount that the provider is allowed to increase their rates under the contract cap. Stated another way, the amount allowed to enforce is how much in excess of the contract caps did the provider go over; anything in excess of the cap, the provider is allowed to enforce and recuperate. For example, for every unique billing code, control can calculate and/or retrieve: (i) the total charge since the last CMI 328, (ii) the number of units since the last CMI 334, (iii) the unit charge before the CMI, and (iv) a Chargemaster Protection Language ("CPL") percent. Control then calculates what the insurer would have paid without a chargemaster increase using Eq. 2 as follows:

$$\text{Payment Absent CMI} = \text{Unit Charge Before CMI} \times \text{Unit Charge After CMI} \qquad \text{Eq. 2}$$

Control then calculates what the total amount the insurer would allow the provider to charge using Eq. 3 as follows:

$$\text{Amount Allowed to Charge} = (1 + \text{CPL Percent}) \times \text{Payment Absent CMI} \qquad \text{Eq. 3}$$

In some embodiments, contracts between the provider and the insurer may include CPL. The CPL includes contract caps such as one or more of billing code rate caps, service category rate caps, sub-category rate caps, and provider category rate caps. The CPL may be represented by a percentage. For example, if a contract has a billing code rate cap of 5%, the CPL percentage may be 5%. The CPL may also include what the insurer can do when any particular cap is violated or exceeded. Control then calculates the Amount Allowed to Enforce ("AAE") for each billing code in the category using the total charge since the last CMI 328 ("$C_{totalCMI}$") and the amount allowed to charge ("AAC"), using Eq. 4 as follows:

$$\text{AAE} = C_{totalCMI} - \text{AAC} \qquad \text{Eq. 4}$$

Control calculates the weighted CMI by charges 340 ("wCMI") for each billing code in the category using the CMI percent increase 326 ("IncCMI") for a particular billing code, the total charge since the last CMI 328 ("$C_{totalCMI}$") for the particular billing code, and the sum 342 ("$\Sigma C_{totalCMI}$") of the total charges since the last CMI 328 for all the billing codes in the category, using Eq. 5 as follows:

$$wCMI = IncCMI \times \frac{C_{totalCMI}}{\sum C_{totalCMI}} \qquad \text{Eq. 5}$$

Control can then calculate the sum 344 of the weighted CMI by charges 340 for the category by summing the weighted CMI by charges 340 for each billing code in the category.

One or more levels of sub-category CMI roll up data may be calculated using the same equations as the category CMI roll up data, where the billing codes are grouped into one or more sub-categories. Control may generate a sub-category CMI roll up data table and, in some embodiments, the sub-category CMI roll up data table may be presented in a user interface by the user device 134 to an operator. The provider CMI roll up data may be calculated using the same equations as the category CMI roll up data, where the billing codes are grouped by provider. Control may generate a provider CMI roll up data table and, in some embodiments, the provider CMI roll up data table may be presented in a user interface by the user device 134 to an operator.

In some embodiments, billing code-level data can be rolled up to a sub-category level, sub-category-level data can be rolled up to a category level, and category-level data can be rolled up to a provider level. For example: (i) in the roll up from the billing code level to the sub-category, the data in FIG. 19 is at a billing code level, (ii) in the roll up from the sub-category level to the category level, the data in FIG. 19 is at the sub-category level, (iii) in the roll up from the category level to the provider level, the data in FIG. 19 is at the category level.

Figure 4:
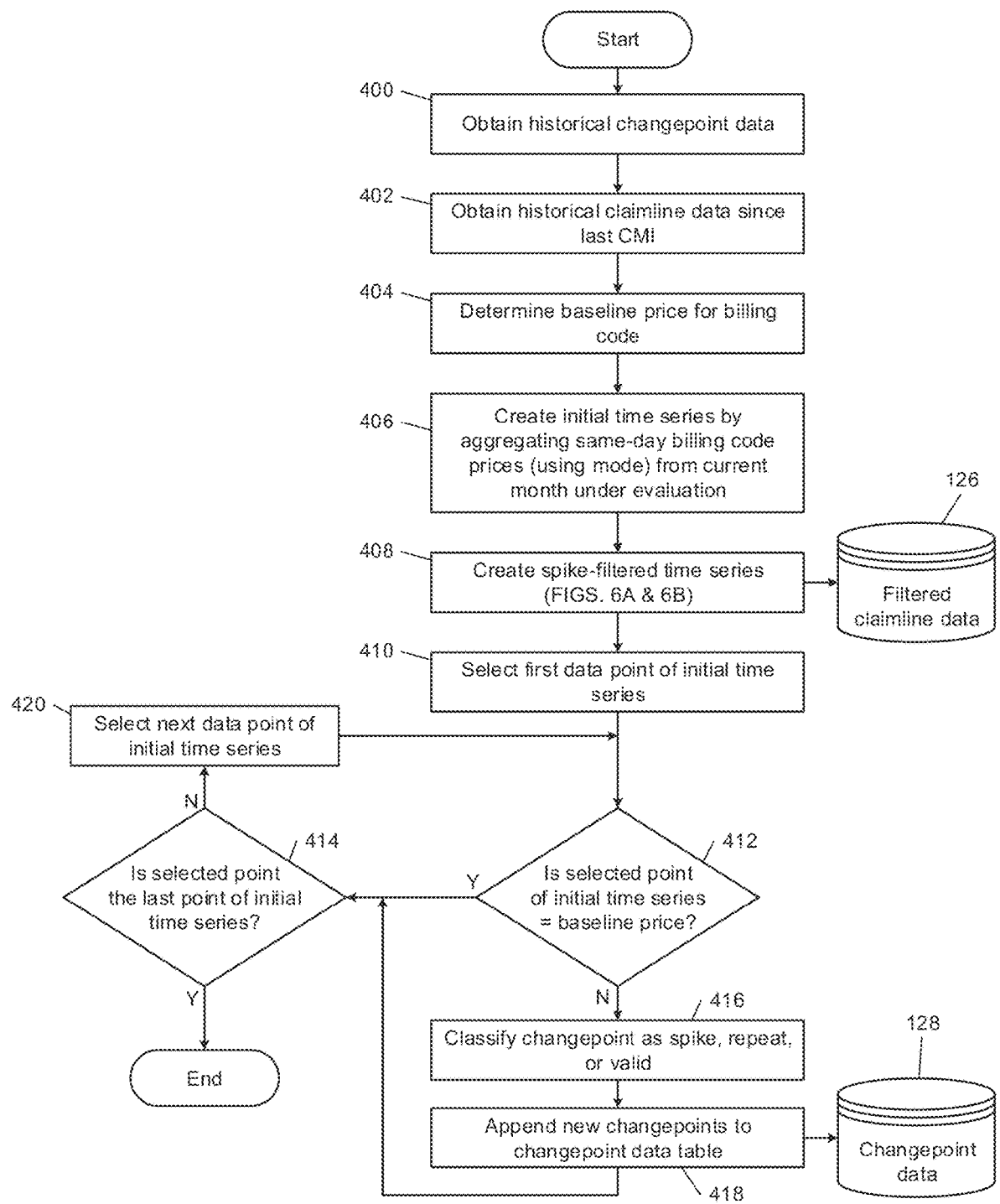
FIG. 4 is a flowchart of an example of an analysis for identifying a changepoint for a billing code based on claimline data according to the principles of the present disclosure.

FIG. 4 is a flowchart of an example of an analysis for identifying a changepoint for a billing code based on claim-line data. At 400, control obtains historical changepoint data 128 for the billing code from the output data store 116, wherein the changepoint data 128 includes the billing code value since the last changepoint for that billing code. At 402, control obtains historical claimline data since the last CMI for the provider. At 404, control determines the baseline price for the billing code. The baseline price may be determined by using mode to identify the most-commonly billed price for the billing code in the historical claimline data for the time period between the last changepoint date and the month prior to the current month under evaluation. For example, assume the current month under evaluation is July and the last changepoint for the billing code was on April 15, when the price of the billing code increased to $100. Control evaluates historical claimline data from April 15 (the changepoint date) through June 30 (the last day of the month prior to the current month under evaluation). Assuming control determines, using mode, that the most-commonly billed price for the billing code during that time period is $100, then the baseline price for the billing code is $100. Control does not include claimline data for the current month under evaluation in determining the baseline price of the billing code.

At 406, control aggregates same-day billing code prices (using mode) for the billing code from 306 to create an initial time series of billing code prices from the current month under evaluation. Creating a time series of billing code prices from the claimline data for each specific billing code allows control to capture the differences in price for each billing code. In some embodiments, aggregation of the billing code prices can be a monthly aggregation or can be a multi-day average aggregation. At 408, control creates a spike-filtered time series from the initial time series, as described in further detail with respect to FIGS. 6A and 6B. The spike filtered claimline data can then be stored as the filtered claimline data 126 in the output data store 116. At 410, control selects the first data point of the initial time series of the current month under evaluation. At 412 control compares the billing code price in the initial time series to the baseline price for the billing code to determine whether a changepoint has occurred during the current month under evaluation. In certain instances, there may be multiple changepoints within a month. If the billing code price is equal to the baseline price, then there is no changepoint and control proceeds to 414. However, if the billing code price is not equal to the baseline price, then a changepoint has occurred and control proceeds to 416. At 416, control determines whether the changepoint is a spike, a repeat, or a valid changepoint. If the billing code price was flagged as a spike from the spike filter at 402, then control classifies the changepoint as a spike. If the billing code price is not equal to the baseline price, but repeats on a subsequent date following a claim where the billing code price was at the baseline price, then the changepoint is classified as a repeat. If the billing code price is not equal to the baseline price, but is not classified as a spike or a repeat, then the billing code price is classified as a valid changepoint. At 418, control appends the data regarding the classified changepoints to the changepoint data 128, including one or more of the billing code, the price at the changepoint for the billing code, the date of the changepoint, and the classification (repeat, spike, or valid). After 418, control proceeds to 414 where control determines whether the selected point is the last point of the initial time series. If the selected point is the last point of the initial time series, then control ends; otherwise, control proceeds to 420. At 420, control selects the next data point in the initial time series for the current month under evaluation. After 420, control returns to 412.

Figure 5:
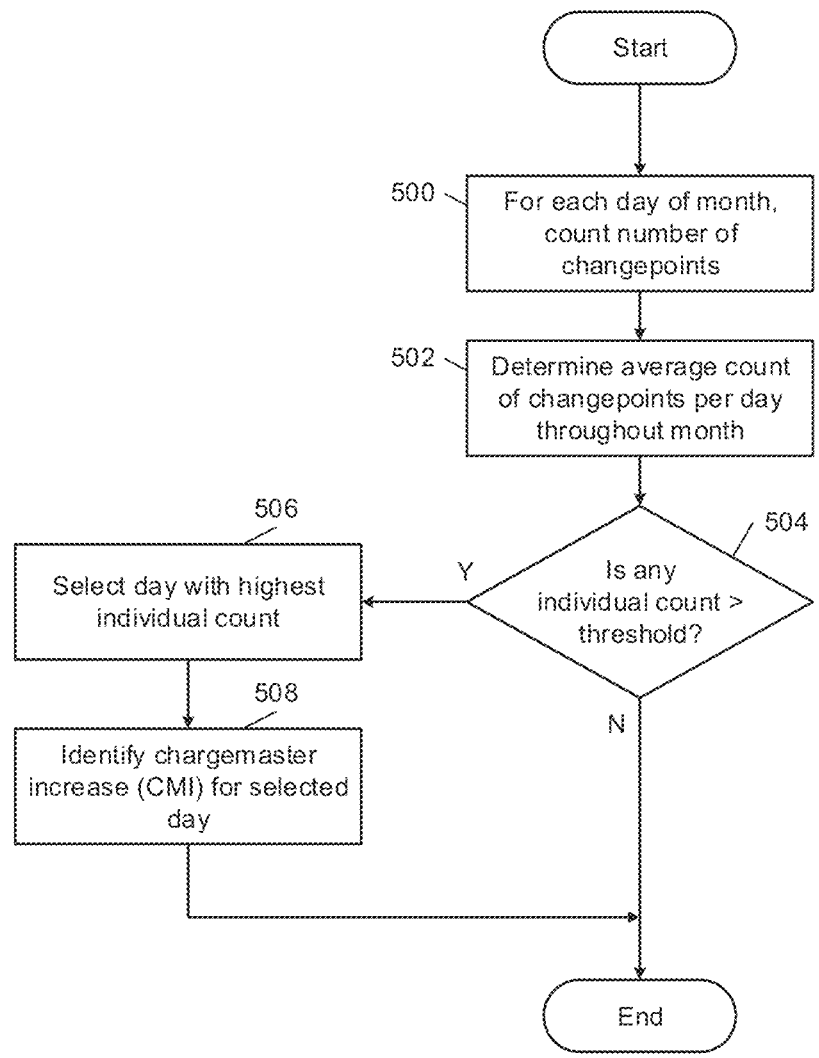
FIG. 5 is a flowchart of an example of an analysis for identifying a provider chargemaster increase based on changepoints according to the principles of the present disclosure.

FIG. 5 is a flowchart of an example of an analysis for identifying a provider chargemaster increase based on changepoints. At 500, control counts the number of changepoints for all billing codes for the provider for each day of the current month under evaluation. At 502, control determines a statistical parameter of changepoints per day. The statistical parameter may be the arithmetic mean (average), the median, or the mode. For example, in some embodiments, the statistical parameter is the average. At 504, control determines whether the maximum number of changepoints on any given day exceeds the statistical parameter of changepoints per day by a certain threshold. In some embodiments, the statistical parameter of changepoints may be calculated using changepoint data from one or more prior months. If the threshold is exceed, control can infer that a chargemaster increase has occurred and, accordingly, the provider has increased their prices. If the threshold is exceeded, control continues to 506; otherwise, control ends. In some embodiments, the threshold may be three times the statistical parameter of changepoints per day. In some embodiments, the threshold may be two times the statistical parameter of changepoints per day. In some embodiments, the threshold may be 2.5 standard deviations (2.5σ) above the statistical parameter of changepoints per day. In some embodiments, the threshold may be different for different providers. In some embodiments, the threshold may be empirically determined based on historical claimline data and may be updated as control analyzes new claimline data. At 506, control selects the day with maximum count of changepoints. At 508, control identifies a chargemaster increase for the day selected at 506 for the provider. By performing a time-series analysis of prices for one or more billing codes, control is able to infer that a provider has increased the prices in its chargemaster by correlating a certain number of changepoints for billing codes in claimline data to a chargemaster increase.

Figure 6A:
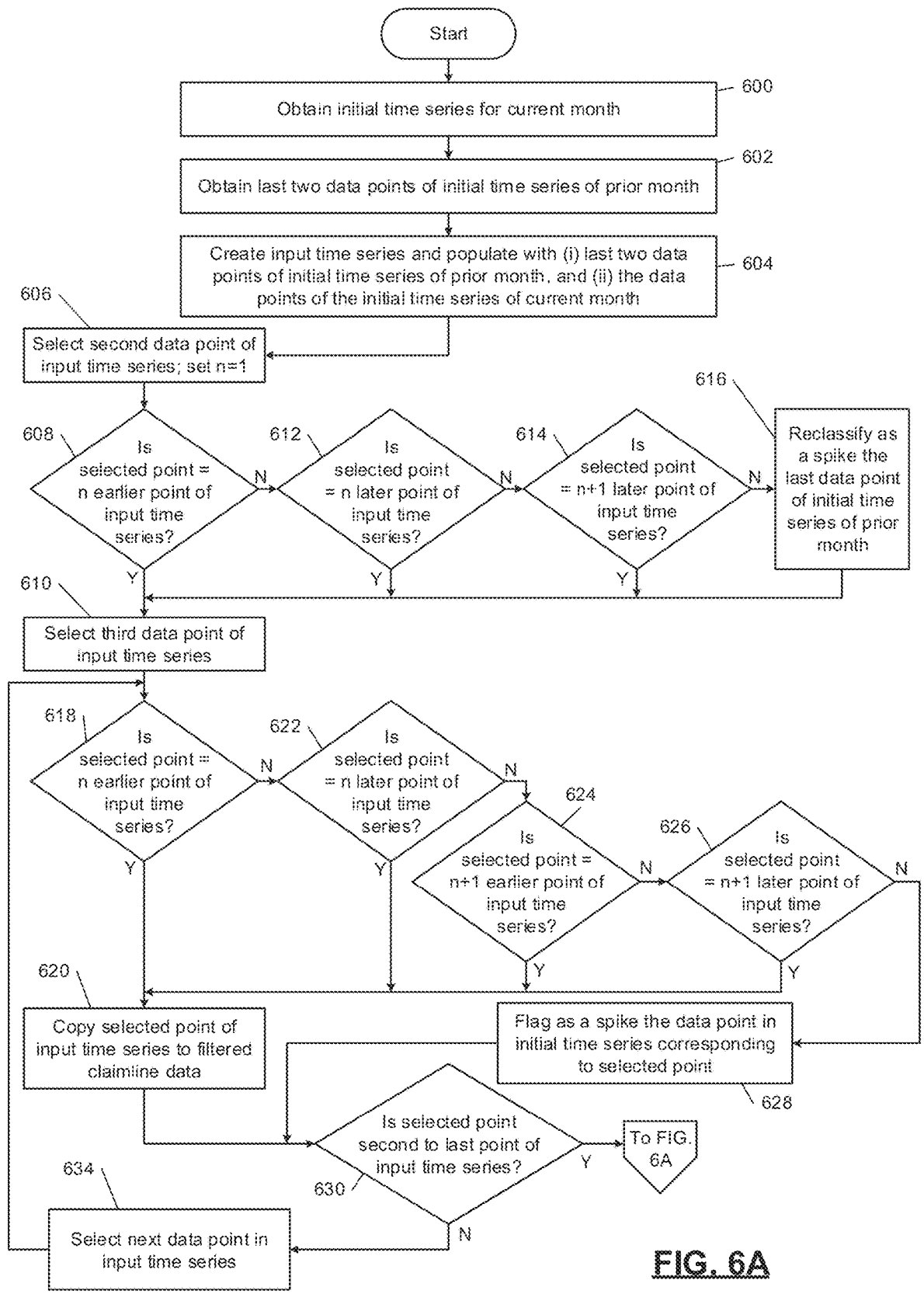
FIGS. 6A and 6B together are a flowchart of an example of a spike filter to filter spikes in billing code prices in the time-series data according to the principles of the present disclosure.
Figure 6B:
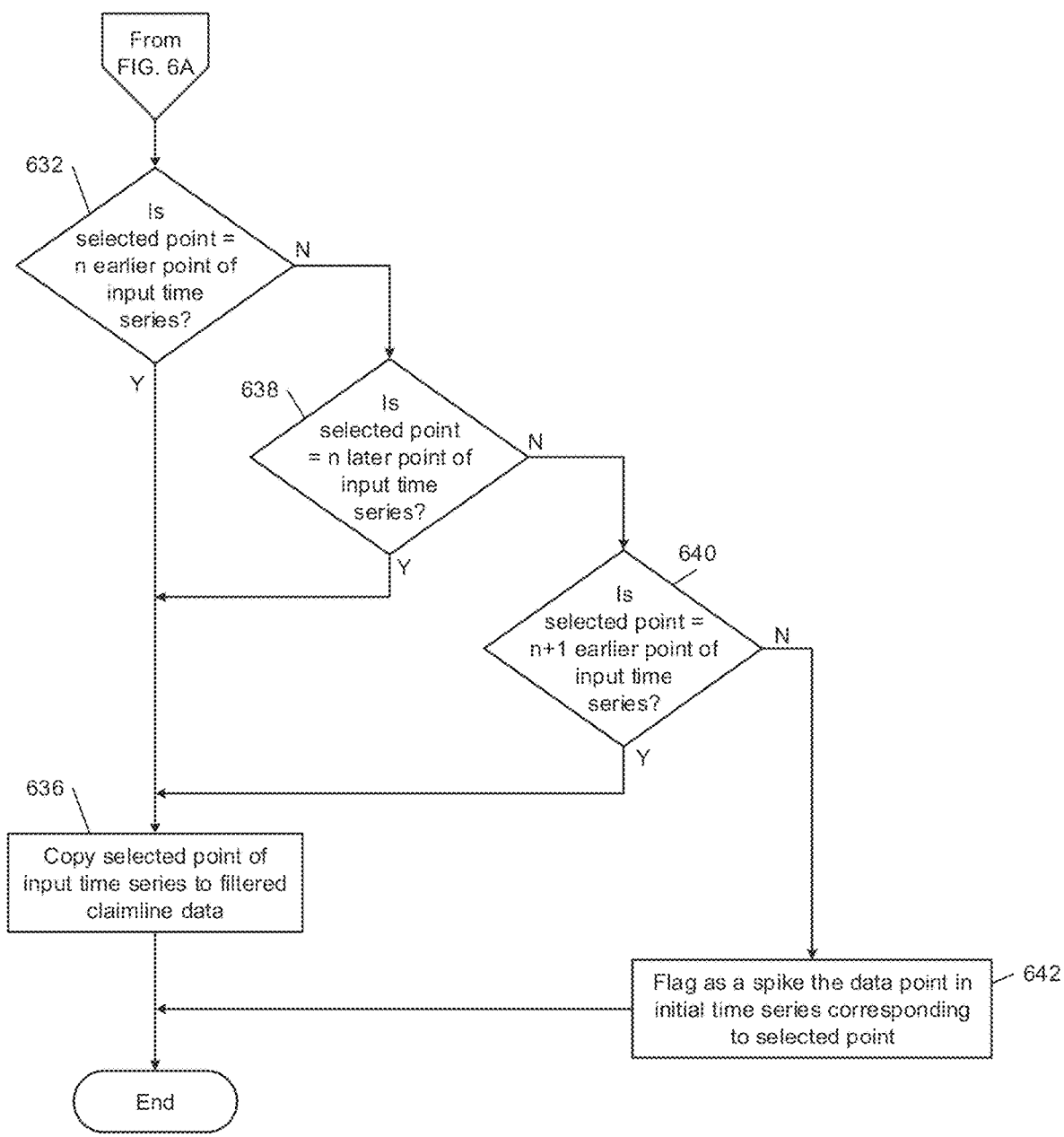
Figure 7:
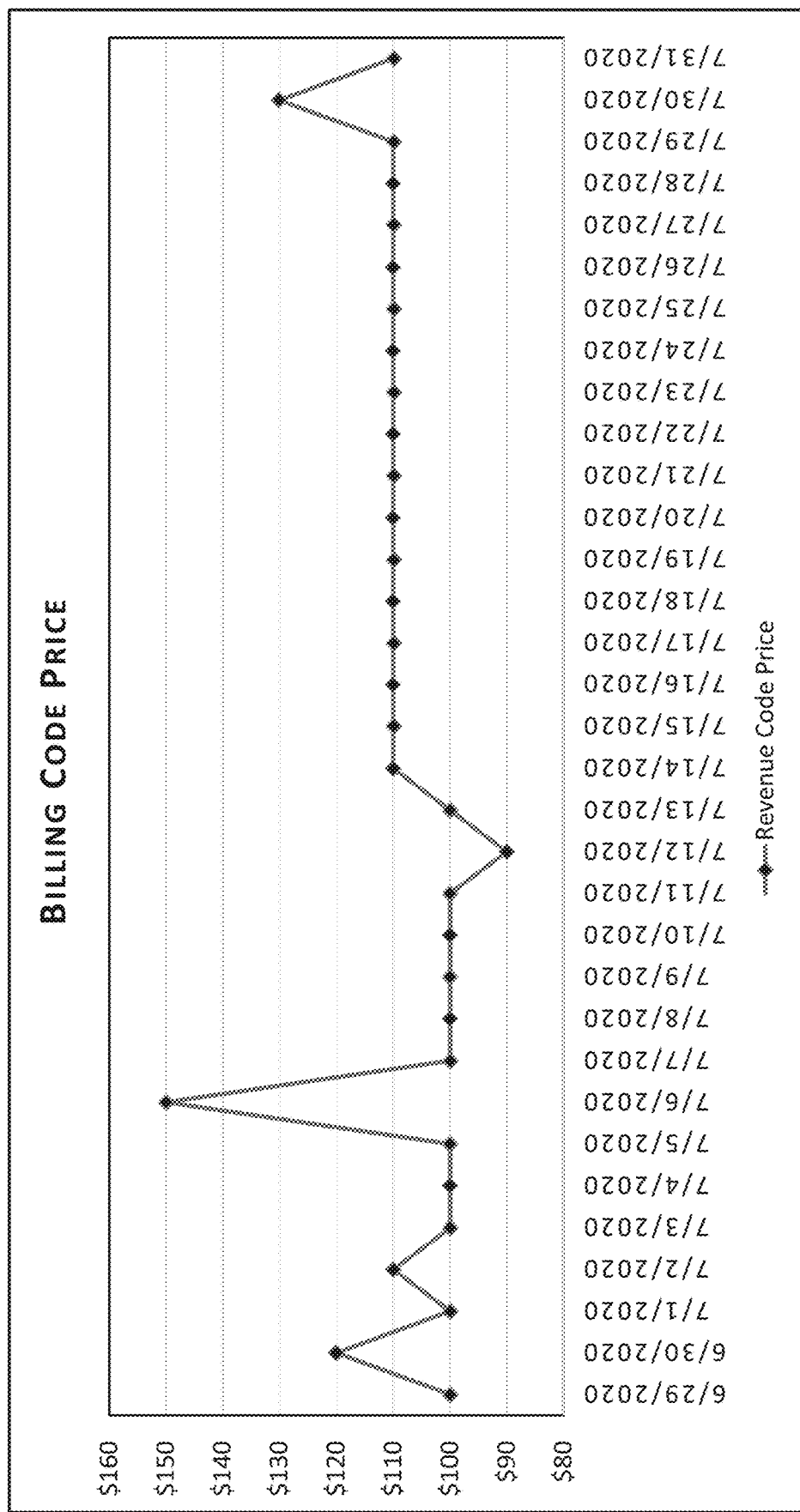
FIG. 7 is a chart showing an example time-series data.

FIGS. 6A and 6B together are a flowchart of an example of a spike filter to filter spikes in billing code prices in the time-series data from 400. The data points in the time-series data represent prices for a billing code. FIG. 7 is a chart showing an example time-series data. In particular, the spike filter is configured to filter out and flag anomalous prices for billing codes found in the time-series data. For example, if a billing code is being consistently billed at $100, is then billed at $150, and then is billed again at $100, the spike filter can flag the $150 charge as a spike. The spike filter can create a filtered time-series data that does not include any spikes. Filtering out the spikes in the time-series data allows for the proper classifications of changepoints in the claimline data.

In FIG. 6A, at 600, control obtains the initial time series from 400 for the current month under evaluation. It is possible that the price of a billing code increases in the last data point of a month. If the price of the billing code remains the same at the beginning of the next month, then the increase may be a valid changepoint. However, if the price of the billing code returns to the price prior to the last data point of the month, then the increase may be a spike. To filter and classify the last data point of a month, the spike filter looks back to the initial time series from the month immediately prior to the current month under evaluation. At 602, control obtains the last two data points of the initial time series of the prior month.

At 604, control creates an input time series for use by the spike filter. Control also populates the input time series with the last two data points of the initial time series of the prior month obtained at 602 and the data points of the initial time series of the current month under evaluation obtained at 600. The first two data points of the input time series are the last two data points of the initial time series of the prior month, the third data point of the input time series is the first data point of the initial time series of the current month under evaluation, and the remaining data points of the input time series are the remaining data points of the initial time series of the current month under evaluation. Each data point in the input time series is the price of the billing code on a particular date. Thus, where the spike filter is determining whether a selected data point is equal to one or more preceding or one or more subsequent data points, the spike filter is comparing the prices of the billing codes in the data points.

In some embodiments, the input time series may be stored in the output data store 116. In some embodiments, the input time series may be temporarily stored in memory during filtering and flagging by the spike filter.

At 606, control selects the second data point in the input time series (i.e., the last data point in the initial time series of the prior month) and control sets n equal to 1. At 608, control determines whether the selected point is equal to the n earlier data point in the input time series (i.e., the second to last data point in the initial time series of the prior month). If so, control proceeds to 610; otherwise control proceeds to 612. At 612, control determines whether the selected point is equal to the n later point in the input time series (i.e., the first data point of the initial time series of the current month under evaluation). If so, control proceeds to 610; otherwise, control proceeds to 614. At 614, control determines whether the selected point is equal to the n+1 later point in the input time series. If so, control proceeds to 610; otherwise, control proceeds to 616. At 616, in response to a determination by control that the selected data point is not equal to the n+1 later point in the input time series, control reclassifies as a spike the last data point of the initial time series of the prior month. Thus, if the selected data point is not equal to any of the data points evaluated at 608, 612, or 614, then the data point in the initial time series of the prior month corresponding to the selected data point of the input time series is flagged as a spike. Control then proceeds to 610. However, if the selected data point is equal to any of the data points evaluated at 608, 612, or 614, then control proceeds to 610.

For example, in FIG. 7, if the current month under evaluation is July, then control obtains data from June 29 and June 30. Control selects the billing code price of $120 on June 30 and compares it to the billing code price of $100 on June 29. Control then determines that the billing code prices on June 30 and June 29 are not equal. Control then compares the billing code price of $120 on June 30 with the billing code price of $100 on July 1. Control then determines that the billing code prices on June 30 and July 1 are not equal. Control then compares the billing code price of $120 on June 30 with the billing code price of $110 on July 2. Control then determines that the billing code prices on June 30 and July 2 are not equal. Control then reclassifies the billing code price of $120 on June 30 as a spike.

Returning to FIG. 6A, at 610, control selects the second data point in the input time series (i.e., the first data point in the initial time series of the current month under evaluation). At 618, control determines whether the selected point is equal to the n earlier point in the input time series. If so, control proceeds to 620; otherwise, control proceeds to 622. At 622, control determines whether the selected point is equal to the n later point in the input time series. If so, control proceeds to 620; otherwise, control proceeds to 624. At 624, control determines whether the selected point is equal to the n+1 earlier point in the input time series. If so, control proceeds to 620; otherwise, control proceeds to 626. At 626, control determines whether the selected point is equal to the n+1 later point in the input time series. If so, control proceeds to 620; otherwise, control proceeds to 628.

In summary, at 618 and 622, control compares the selected point to the immediately preceding and following data points. Depending on the outcome of those comparisons, control proceeds to 624 and 626, where control compares the selected point to the data point that is two data points before and the data point that is two data points after the selected data point.

At 628, in response to a determination by control that the selected data point is not equal to the n+1 later point in the input time series, control flags as a spike the data point in the initial time series corresponding to the selected data point of the input time series. Thus, if the selected data point is not equal to any of the data points evaluated at 618, 622, 624, or 626, then the data point in the initial time series corresponding to the selected data point of the input time series is flagged as a spike at 628. Control then proceeds to 630. However, if the selected data point is equal to any of the data points evaluated at 618, 622, 624, or 626, then at 620, control copies the selected data point of the input time series to the filtered claimline data 126.

With reference again to FIG. 7, following the above analysis, control would determine and flag the billing code price of $110 on July 2, the billing code price of $150 on July 6, and the billing code price of $90 on July 12 as spikes. Additionally, following the above analysis, control would determine that the billing code price increase from $100 to $110 on July 14 is not a spike and would copy the billing code price of $110 on July 14 to the filtered claimline data 126.

Returning again to FIG. 6A, after control either copies the selected point to the filtered claimline data 126 or flags data point in the initial time series corresponding to the selected point as a spike at 620 and 628, respectively, control then proceeds to 630. At 630, control determines whether the selected point is the second to last data point in the input time series. If so, control proceeds to 632 in FIG. 6B; otherwise, control proceeds to 634. At 634, control selects the next data point in the input time series and then returns to 618.

Referring now to FIG. 6B, control determines whether the second to last point in the input time series is a spike. At 632, control determines whether the selected point is equal to the n earlier point of the input time series. If so, control proceeds to 636; otherwise, control proceeds to 638. At 638, control determines whether the selected point is equal to the n later point in the input time series, which at this part of the analysis is the last data point in the input time series. If so, control proceeds to 636; otherwise, control proceeds to 640. At 640, control determines whether the selected point is equal to the n+1 earlier point in the input time series. If so, control proceeds to 636; otherwise, control proceeds to 642. At 642, in response to a determination by control that the selected data point is not equal to the n+1 earlier point in the input time series, control flags as a spike the data point in the initial time series corresponding to the selected data point as a spike. Thus, if the selected data point is not equal to any of the data points evaluated at 632, 638, or 640, then the data point in the initial time series corresponding to the selected data point is flagged as a spike at 642. However, if the selected data point is equal to any of the data points evaluated at 632, 638, or 640, then at 636, control copies the selected data point of the input time series to the filtered claimline data 126. With reference again to FIG. 7, following the above analysis, control would determine and flag the billing code price of $130 on July 30 as a spike.

FIGS. 8A, 8B, 8C, and 8D together are a flowchart of an example of the listener module 114 that monitors for alerts from the alert module 110. In particular, FIGS. 8A, 8B, 8C, and 8D are flowcharts of an example of an analysis for enforcing a cap on the chargemaster for variable rates.

At 800, control begins listening for alerts from the alert module 110. In some embodiments, control may subscribe to a Kafka topic to listen for and receive alerts from the alert module 110. At 802, control determines whether an alert has been published by the alert module 110. In some embodiments, the alert published at 218 (FIG. 2) contains the provider name and information at the billing code level (e.g., billing code, baseline price, price at the changepoint, changepoint date, etc.). In some embodiments, the alert published at 218 (FIG. 2) includes additional information. For example, the alert can contain the provider name, billing code-level information, service category-level information, and provider category-level information. The service category-level information may include the average baseline price, the average price at the changepoint, and the changepoint date, for one or more service categories (e.g., Surgery, Emergency Room, Diagnostic, Drugs, DME, etc.). The service category-level information in the alert may be the result of the aggregation and average calculation at 322 (FIG. 3). The provider category-level information may include the average baseline price, the average price at the changepoint, and the changepoint date, for one or more provider categories (e.g., Inpatient, Outpatient). The provider category-level information in the alert may be the result of the aggregation and average calculation at 324 (FIG. 3).

If an alert is published, control proceeds to 804; otherwise control returns to 802 and waits for an alert to be published. At 804, control determines whether a smart contract is enabled between the insurer and the provider. If so, control proceeds to 806; otherwise, control ends. At 806, control selects the first billing code in the alert. At 808, control extracts the discount corresponding to the selected billing code from the contract between the insurer and the provider. In some embodiments, control may extract the discount from the contract data 124 stored in the input data store 120 via the data retrieval module 106 or via an API call.

At 810, control extracts the billing code rate cap corresponding to the selected billing code from the contract. The billing code rate cap allows the provider to increase the price for the billing code by the cap amount and the provider will still pay up to the cap. For example, assume the baseline price for billing code 00002 was $100, the contract states that the insurer will pay billing code 00002 at a 10% discount, and the contract includes a billing code rate cap of 5%. In the absence of a billing code rate cap, the insurer would pay $90 (10% off of $100) for billing code 00002. But with the billing code rate cap of 5%, if the provider increases the price for billing code 00002 from $100 to $105, then the insurer would pay a 10% discount off of $105 for a total of $94.50 ($105−10%×$105=$94.50). The insurer would not pay more than $94.50 for billing code 00002.

At 812, control calculates the percent increase of the price at the changepoint compared to the baseline price for the selected billing code. Continuing with the example above, if the alert indicates a changepoint increase in the price for billing code 00002 from $100 (baseline price) to $120 (price at the changepoint), control determines a 20% increase in the price for billing code 00002 (($120−$100)/$100× 100=20%). At 814, control determines whether the percent increase in the price at the changepoint for the billing code is greater than the allowed percent increase under the billing code rate cap. Continuing with the example above, control compares the 20% increase in the price for billing code 00002 to the 5% increase allowed under the billing code rate cap. If control determines that the percent increase in the price at the changepoint for the billing code is greater than the allowed percent increase under the billing code rate cap, control proceeds to 816; otherwise, control proceeds to 818.

At 816, control calculates an adjusted discount for the billing code. By adjusting the discount for the billing code, the insurer can ensure that it does not pay more for the billing code than is allowed by the contracted billing code rate cap. The adjusted discount can be calculated using Eq. 6 and Eq. 7 as follows:

$$\text{Adjusted discount} = \left(1 - \frac{\text{Max price}}{\text{Current price}}\right) \times 100; \qquad \text{Eq. 6}$$

The Max price is calculated as follows:

Max price=Baseline price×(1+Rate cap)×(1−Discount);          Eq. 7

The Current price is the price at the changepoint of the billing code included in the alert, the Baseline price is the baseline price of the billing code included in the alert, and the Rate cap and Discount corresponding to the billing code are specified in the contract with the provider. Again referring to the example for billing code 00002 above, where the baseline price is $100, the contracted billing code rate cap is 5%, and the contracted discount is 10%, the Max price according to Eq. 7 would be as follows: Max price=$100× (1+0.05)×(1−0.10)=$94.50. If the price at the changepoint for billing code 00002 as reflected in the alert for the changepoint increase is $120, then the Adjusted discount according to Eq. 6 would be as follows: Adjusted discount= (1−$94.50/$120)×100=21.25%. Thus, applying this adjusted discount of 21.25% to the price at the changepoint of $120 for billing code 00002, the insurer would still only pay $94.50.

After calculating the adjusted discount at 816 for the selected billing code, at 818, control determines whether there is another billing code in the alert. If so, control selects the next billing code in the alert at 820 and returns to 808; otherwise control proceeds to 822 in FIG. 8B.

Figure 8A:
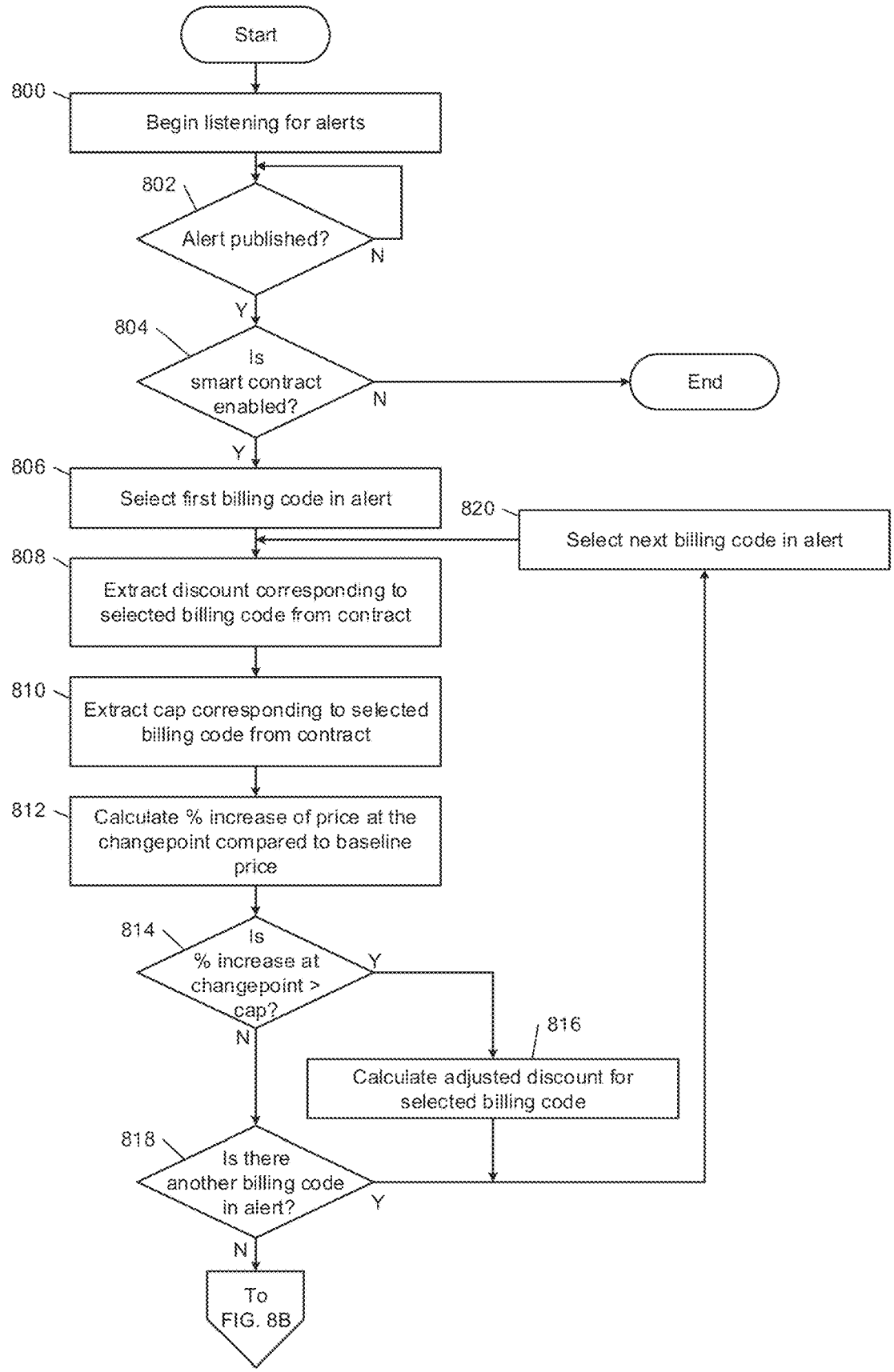
FIGS. 8A, 8B, 8C, and 8D together are a flowchart of an example of a listener module that monitors for alerts from an alert module according to the principles of the present disclosure.
Figure 8B:
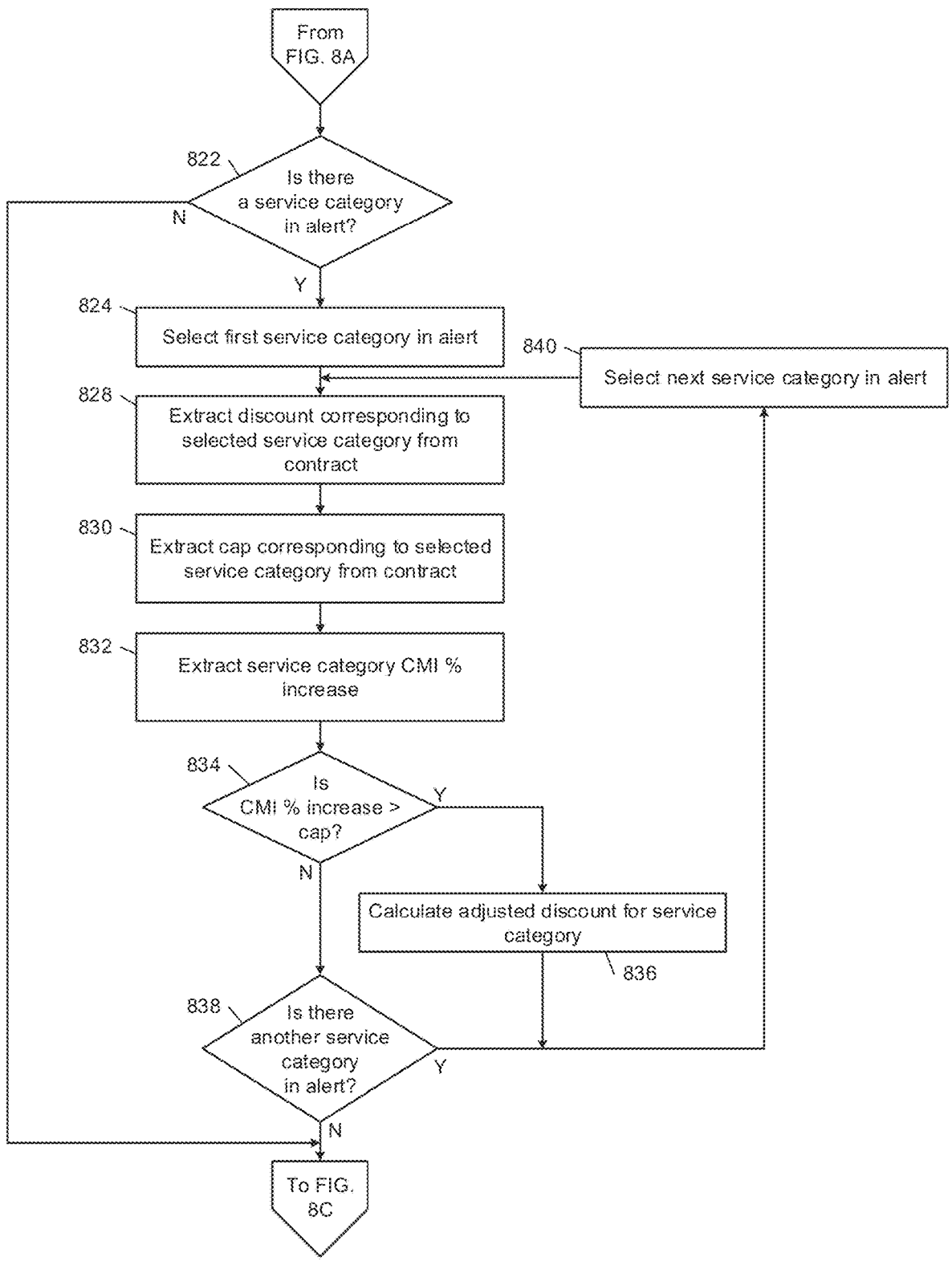

Now in FIG. 8B, at 822, control determines whether there is a service category (e.g., Surgery, Diagnostic, Drugs, DME, etc.) in the alert. If so, control proceeds to 824; otherwise control proceeds to 826 in FIG. 8C. At 824, control selects the first service category in the alert. At 828, control extracts the discount corresponding to the selected service category from the contract between the insurer and the provider. In some embodiments, control may extract the contracted discount from the contract data 124 stored in the input data store 120 via the data retrieval module 106 or via an API call.

At 830, control extracts the service category-level rate cap corresponding to the selected service category from the contract. Similar to the billing code rate cap, the service category-level rate cap allows the provider to increase prices for billing codes within the service category by the cap amount and the provider will still pay up to the cap. For example, a contract may have a 5% cap on the surgery service category.

At 832, control extracts the service category CMI percent increase from the multi-level metric data 130, where the service category CMI percent increase is the sum 344 of the weighted CMI by charges 340 for the selected service category. At 834, if control determines that the CMI percent increase for the service category is greater than the allowed percent increase under the service category rate cap, control proceeds to 836; otherwise, control proceeds to 838. At 836, control calculates an adjusted discount for the service category. By adjusting the discount for the service category, the insurer can ensure that it does not pay more for the service category than is allowed by the contracted service category rate cap.

After calculating the adjusted discount at 836 for the selected service category, at 838, control determines whether there is another service category in the alert. If so, control selects the next service category in the alert at 840 and returns to 828; otherwise control proceeds to 826 in FIG. 8C. In some embodiments, there may be caps at one or more sub-category levels in addition to or alternative to the category levels. If there is a sub-category level in an alert, control can utilize the same logic as shown in FIG. 8B to determine whether the sub-category CMI percent increase is greater than the sub-category level cap and can calculate an adjusted discount for the sub-category level.

Figure 8C:
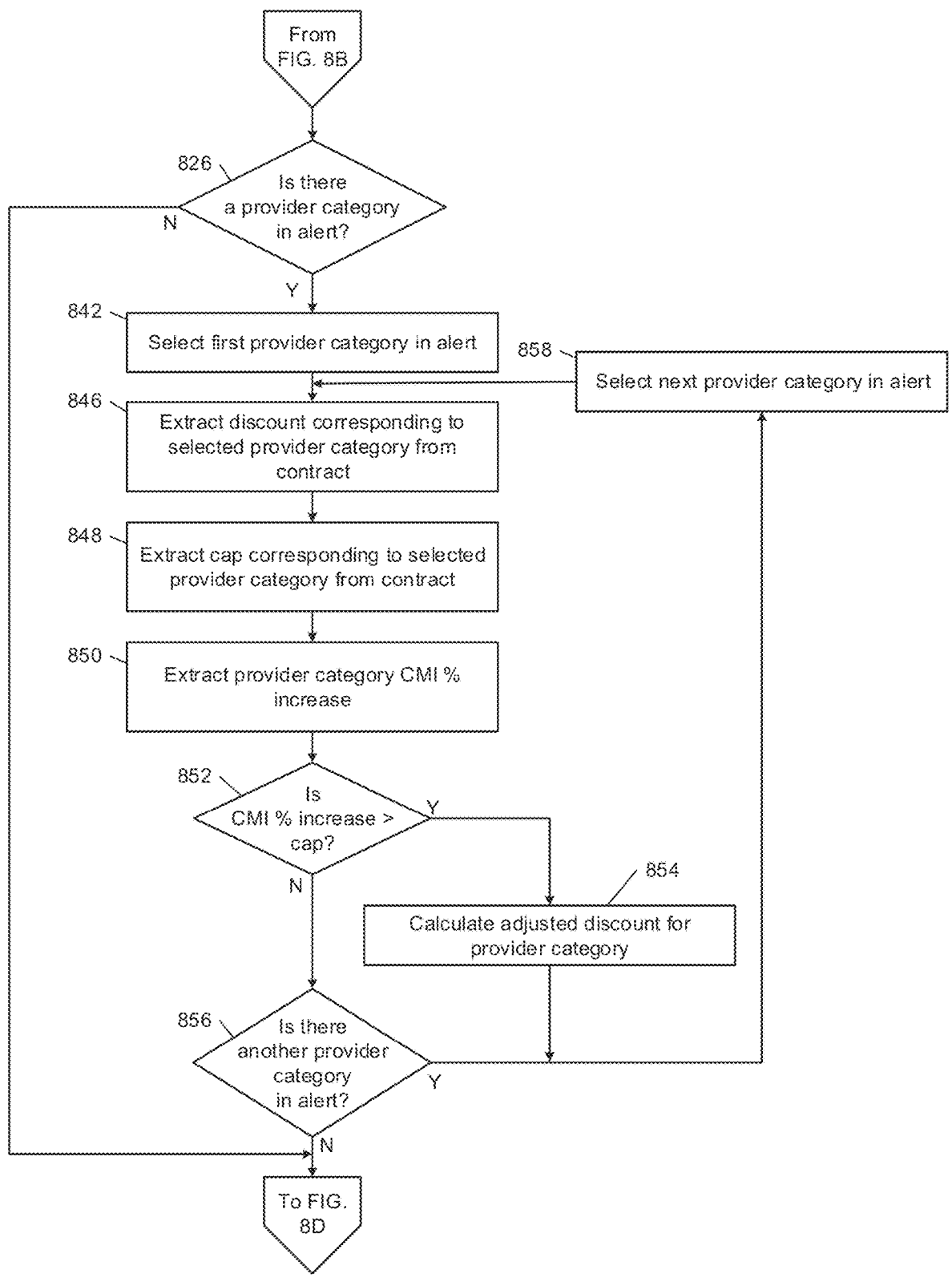

Now in FIG. 8C, at 826, control determines whether there is a provider category in the alert. If so, control proceeds to 842; otherwise control proceeds to 844 in FIG. 8D. At 842, control selects the first service category in the alert. At 846, control extracts the contracted discount from the contract between the insurer and the provider corresponding to the selected provider category (e.g., Inpatient, Outpatient). In some embodiments, control may extract the contracted discount from the contract data 124 stored in the input data store 120 via the data retrieval module 106 or via an API call.

At 848, control extracts the provider category-level rate cap corresponding to the selected provider category from the contract. Similar to the billing code rate cap and the service category-level rate cap, the provider category-level rate cap allows the provider to increase prices for billing codes within the provider category by the cap amount and the provider will still pay up to the cap. For example, a contract may have a 3% cap on the inpatient provider category.

At 850, control extracts the provider category CMI percent increase from the multi-level metric data 130, where the provider category CMI percent increase is the sum of the weighted CMI by charges for the selected provider category. At 852, if control determines that the CMI percent increase for the provider category is greater than the allowed percent increase under the provider category rate cap, control proceeds to 854; otherwise, control proceeds to 856. At 854, control calculates an adjusted discount for the provider category. By adjusting the discount for the provider category, the insurer can ensure that it does not pay more for the provider category than is allowed by the contracted provider category rate cap.

After calculating the adjusted discount at 854 for the selected provider category, at 856, control determines whether there is another provider category in the alert. If so, control selects the next provider category in the alert at 858 and returns to 846; otherwise control proceeds to 844 in FIG. 8D.

Figure 8D:
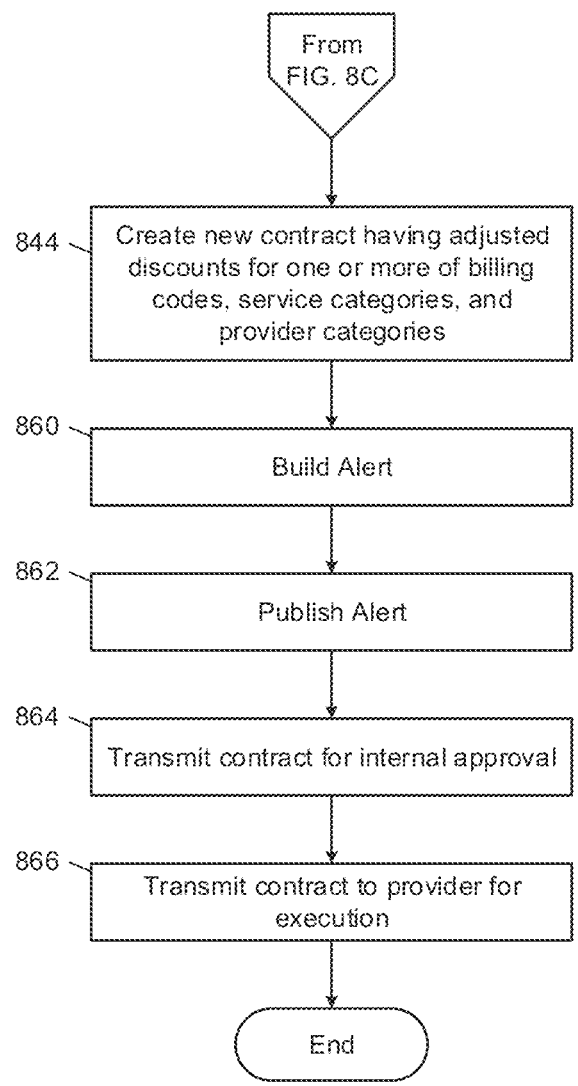

Now in FIG. 8D, after calculating the adjusted discounts at one or more of 816, 836, and 854, control creates a new contract having the adjusted discounts for one or more of billing codes, service categories, and provider categories at 844. At 860, control builds an alert indicating that a new contract has been created. At 862, control publishes the alert created at 860. In some embodiments, the alert may be published in a variety of ways, including but not limited to an email, a text message, an SMS, and/or a push notification. The alert can be displayed to an operator in a user interface on the user device 134. The user interface may be created by the web server 112. At 864, control transmits the contract for internal approval. In some embodiments, control may transmit an alert to the user device 134 that indicates to an operator that a new contract has been prepared. After internal approval of the contract, control transmits the contract to the provider for execution at 866. In some embodiments, 864 may be omitted and control may automatically approve and transmit the contract to the provider. In some embodiments, 866 may be omitted and the contract may be self-executing.

Figure 9:
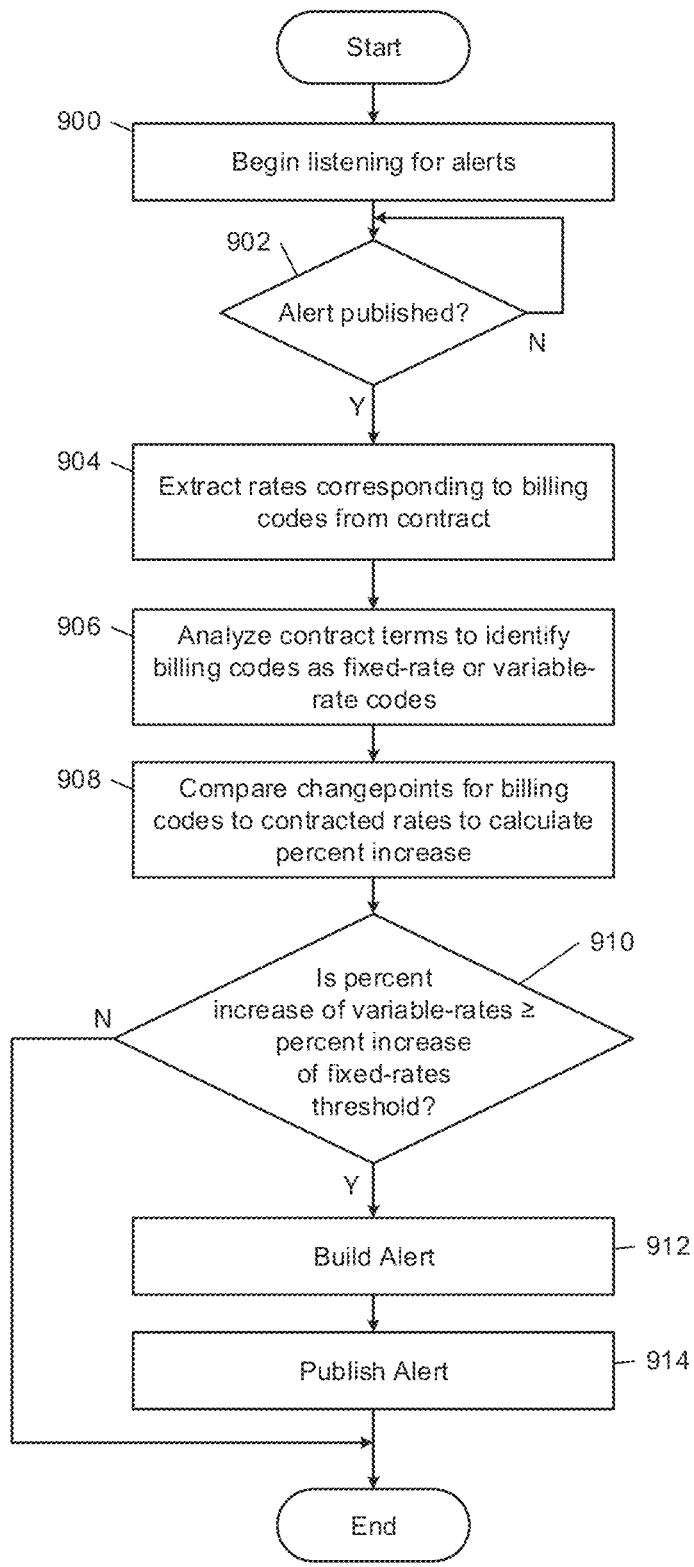
FIG. 9 is a flowchart of another example of a listener module that monitors for alerts from an alert module according to the principles of the present disclosure.

FIG. 9 is a flowchart of another example of the listener module 114 that monitors for alerts from the alert module 110. In particular, FIG. 9 is a flowchart of an example of an analysis for comparing increases of variable-rate billing codes to increases of fixed-rate billing codes. At 900, control begins listening for alerts from the alert module 110. In some embodiments, control may subscribe to a Kafka topic to listen for and receive alerts from the alert module 110. At 902, control determines whether an alert has been published by the alert module 110. In some embodiments, the alert published at 218 (FIG. 2) contains the provider name and information at the billing code level (e.g., billing code, baseline price, price at the changepoint, changepoint date, etc.). If an alert is published, control proceeds to 904; otherwise control returns to 902 and waits for an alert to be published.

At 904, control extracts rates corresponding to the billing codes in the alert from the contract. At 906, control analyzes the contract terms to identify which billing codes are fixed-rate codes or variable-rate codes. At 908, control compares the prices at the changepoints to the baseline prices for the fixed-rate billing codes to calculate a percent increase for the fixed-rate billing codes. Additionally at 908, control compares the prices at the changepoints to the baseline prices for the variable-rate billing codes to calculate a percent increase for the variable-rate billing codes. At 910, control determines whether the percent increase for the variable-rate billing codes is greater than the percent increase for the fixed-rate billing codes. If so, control proceeds to 912; otherwise, control ends. At 912, control builds an alert, and at 914, control publishes the alert. The alert indicates that the percent increase for the variable-rate billing codes is greater than the percent increase for the fixed-rate billing codes. In some embodiments, the alert may be published in a variety of ways, including but not limited to an email, a text message, an SMS, and/or a push notification. The alert can be displayed to an operator in a user interface on the user device 134. The user interface may be created by the web server 112.

A provider may know that for fixed-rate billing codes, they will only be reimbursed by the insurer up to the contracted rate even if they increase the price for the billing code. However, a provider can increase the price for variable-rate billing codes and can get reimbursed a higher amount from the insurer. Thus, an increase in the prices for variable-rate billing codes as compared to the increase (if any) in the prices for fixed-rate billing codes may be indication that a provider may be manipulating the prices of billing codes to increase the amount that the insurer pays to the provider. The listener module 114 of FIG. 9 may alert the insurer to these price increases.

Additionally, the listener module 114 of FIG. 9 may also alert the insurer to an increase in variable-rate billing codes even if the rate caps are not exceeded. For example, for a particular provider if half of the billed billing codes are fixed-rate billing codes and half the billed billing codes are variable-rate billing codes, a 6% increase in the variable-rate billing codes and a 0% increase in the fixed-rate billing codes may appear to only be an overall 3% increase. The 3% increase may be permissible under the contract with the provider; however the 6% increase in variable-rate billing codes may indicate that the provider is attempting to raise prices the prices it can to receive a higher reimbursement.

Figure 10:
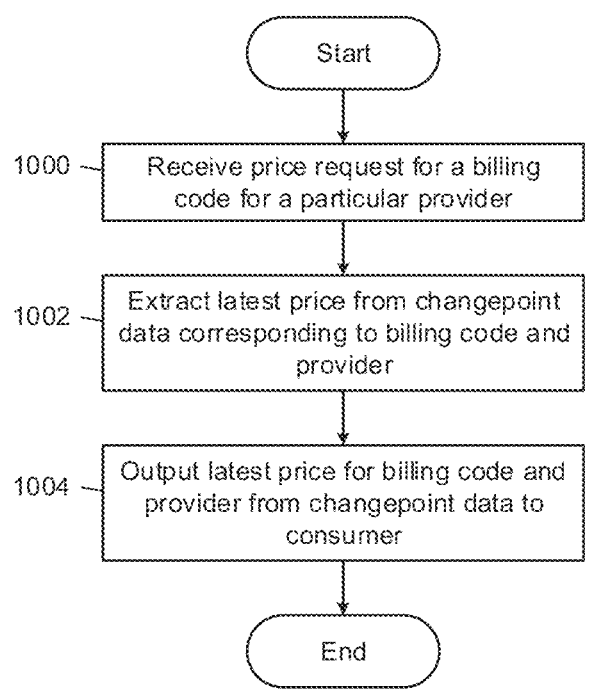
FIG. 10 is a flowchart of an example of a lookup API that may query data from an output data store according to the principles of the present disclosure.

FIG. 10 is a flowchart of an example of the lookup API 118 that may query data from the output data store 116. The analysis in FIG. 10 may be executed when a consumer queries the output data store 116 for a price of one or more billing codes. In some embodiments, the consumer may be an entity within the insurer. In some embodiments, the consumer may be a customer of the insurer. At 1000, control receives a price request for a billing code for a particular provider, for example, via an API call. At 1002, given the received provider and the billing code, control extracts the latest price from the changepoint data 128 corresponding to the billing code for a particular provider. At 1004, control outputs the latest price for the billing code and provider to the consumer. If the consumer is an entity within the insurer, the lookup API 118 may be used to extract changepoint data from the output data store 116 and provide it to a modeling system. The modeling system may use the extracted price data to perform cost forecasting for one or more claims, which may increase the accuracy of modeling a batch of claims.

If the consumer is a customer of the insurer, the lookup API 118 can provide the customer with an estimate of a billing code. For example, in some embodiments, if a customer is needing a knee surgery, the customer can log into their account with their insurer using the user device 134 and the network 136 to request an estimate. The web server 112 can query the lookup API 118 to get estimated prices for the knee surgery (and any related billing codes) from a particular provider. The web server 112 can generate a user interface on the user device 134 that displays the estimated prices for any requested billing code. The customer can select multiple providers in order to obtain multiple estimates for a particular billing code. This may allow the customer to select the provider with the lowest cost option for the billing code.

FIGS. 11-14 are example user interfaces that may be presented by the user device 134 to an operator. FIG. 11 is an example user interface adaptation of a provider summary user interface 1100 that may be presented by the user device 134 to an operator. The provider summary user interface 1100 shows a variety of data for a particular provider (e.g., "Regional Medical Center"). For example, the provider summary user interface 1100 may include a provider findings area 1102, a since last detected CMI area 1104, a contract information area 1106, a detection details area 1108, and a service categories area 1110.

The provider findings area 1102 can identify the detected CMI percentage, a data cleanliness value, the date of surveillance, and the detected CMI date for the selected provider. The since last detected CMI area 1104 can identify various data regarding the provider since the last detected CMI including the total charges, the total charge change impact, the amount allowed to enforce, and the percentage of billing codes included in the aggregation.

The contract information area 1106 can identify the CPL, the current contract effective date, and the next contract effective date for the provider. The detection details area 1108 can identify the number of claimlines, the number of valid changepoints, the number of spikes, and the number of units at the provider level. With reference to FIG. 11, the provider summary user interface 1100 illustrates operation at large scale—for example, that greater than ten thousand claimlines can be processed (in FIG. 11, the number of claimlines depicted is 43,847).

The service categories area 1110 displays various data on one or more service categories (e.g., Surgery, Emergency Room, Diagnostic, Drugs, DME, CT scan, Observation Unit, Nuclear Medicine, etc.) associated with the provider. Each row represents a different service category. Each column displays an attribute of the service category. The service categories area 1110 displays the name 1112 of one or more service categories, the amount allowed to enforce 1114, the CMI percent increase 1116, the total charge change impact 1118, total charges since last CMI 1120, and the number of units 1122 for the displayed one or more service categories. In response to an operator selecting a category name, a subsequent user interface may be presented by the user device 134 to the operator that displays additional information specific to the selected category. For example, in response to an operator selecting "Emergency Room (All Levels)" the user interface shown in FIG. 12 may be presented by the user device 134 to the operator.

FIG. 12 is an example user interface adaptation of a service category summary user interface 1200 that may be presented by the user device 134 to an operator. The service category summary user interface 1200 shows a variety of data for a particular service category (e.g., "Emergency Room (All Levels)"). For example, the category summary user interface 1200 may include a category findings area 1202, a since last detected CMI area 1204, a contract information area 1206, a detection details area 1208, and a sub-categories area 1210.

The category findings area 1202 can identify the detected CMI percentage, a data cleanliness value, the date of surveillance, and the detected CMI date for the selected category. The since last detected CMI area 1204 can identify various data regarding the category since the last detected CMI including the total charges, the total charge change impact, the amount allowed to enforce, and the percentage of billing codes included in the aggregation.

The contract information area 1206 can identify the CPL, the current contract effective date, and the next contract effective date for the provider and/or category. The detection details area 1208 can identify the number of claimlines, the number of valid changepoints, the number of spikes, and the number of units at the category level.

The sub-categories area 1210 displays various data on one or more service sub-categories (e.g., ER Level I, ER Level II, ER Level III, etc.) associated with the category. Each row represents a different service sub-category. Each column displays an attribute of the service sub-category. The service sub-categories area 1210 displays the name 1212 of one or more service sub-categories, the amount allowed to enforce 1214, the CMI percent increase 1216, the total charge change impact 1218, total charges since last CMI 1220, and the number of units 1222 for the displayed one or more service sub-categories. In response to an operator selecting a sub-category name, a subsequent user interface may be presented by the user device 134 to the operator that displays additional information specific to the selected sub-category. For example, in response to an operator selecting "ER Level I" the user interface shown in FIG. 13 may be presented by the user device 134 to the operator.

FIG. 13 is an example user interface adaptation of a service sub-category summary user interface 1300 that may be presented by the user device 134 to an operator. The service sub-category summary user interface 1300 shows a variety of data for a particular service sub-category (e.g., "ER Level I"). For example, the sub-category summary user interface 1300 may include a sub-category findings area 1302, a since last detected CMI area 1304, a contract information area 1306, a detection details area 1308, and a billing code area 1310.

The sub-category findings area 1302 can identify the detected CMI percentage, a data cleanliness value, the date of surveillance, and the detected CMI date for the selected sub-category. The since last detected CMI area 1304 can identify various data regarding the sub-category since the last detected CMI including the total charges, the total charge change impact, the amount allowed to enforce, and the percentage of billing codes included in the aggregation.

The contract information area 1306 can identify the CPL, the current contract effective date, and the next contract effective date for the provider, category, and/or sub-category. The detection details area 1308 can identify the number of claimlines, the number of valid changepoints, the number of spikes, and the number of units at the sub-category level.

The billing code area 1310 displays various data on one or more billing codes (e.g., 99284, 99283, etc.) associated with the category. Each row represents a different service billing code. Each column displays an attribute of the billing code. The billing code area 1310 displays the name 1312 of one or more billing codes, a description of the billing code 1314, the amount allowed to enforce 1316, the CMI percent increase 1318, the total charge change impact 1320, total charges since last CMI 1322, and the number of units 1324 for the displayed one or more billing codes. In response to an operator selecting a billing code, a subsequent user interface may be presented by the user device 134 to the operator that displays additional information specific to the selected billing code. For example, in response to an operator selecting "99284" the user interface shown in FIG. 14 may be presented by the user device 134 to the operator.

Figure 14:
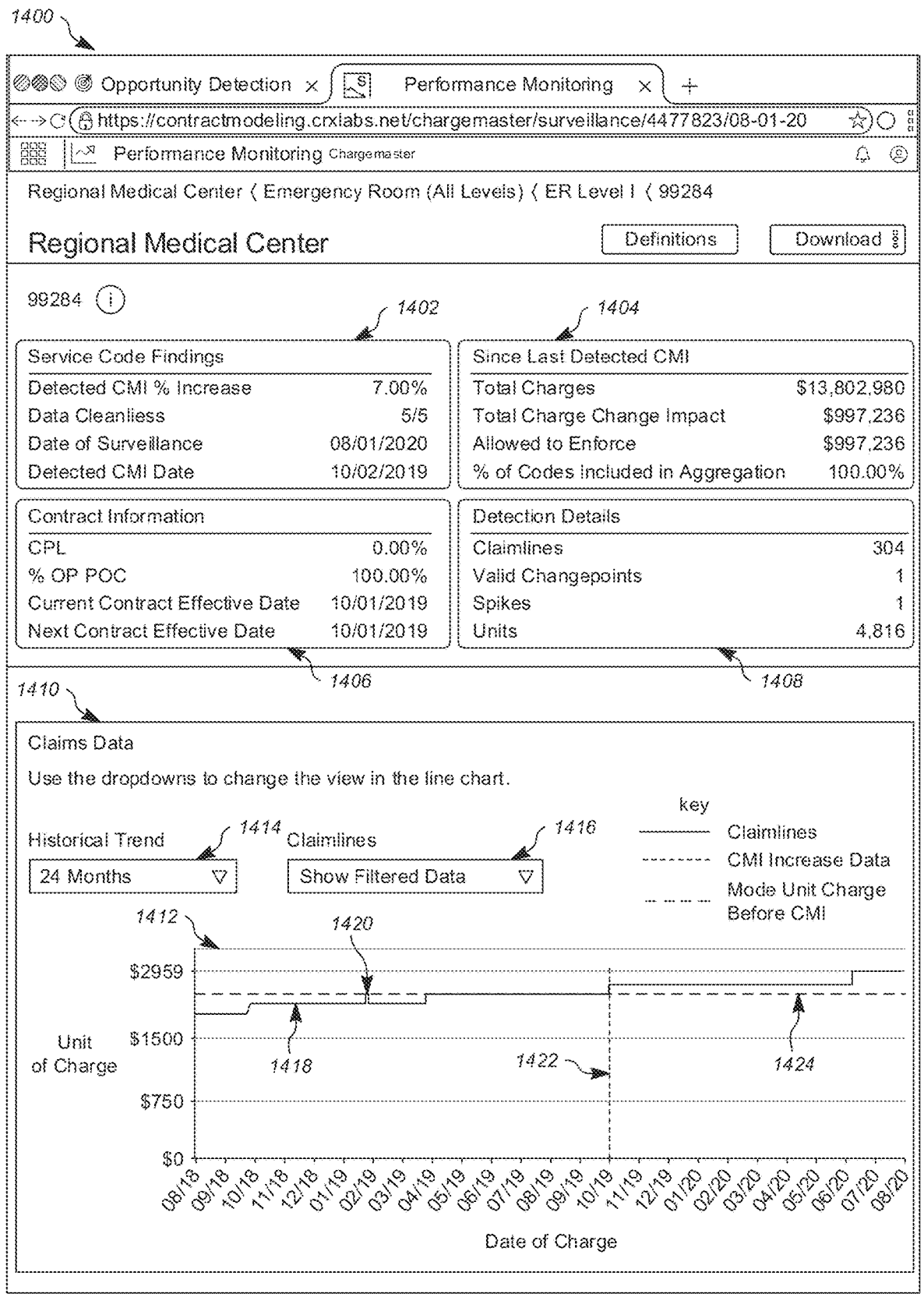

FIG. 14 is an example user interface adaptation of a billing code summary user interface 1400 that may be presented by the user device 134 to an operator. The billing code summary user interface 1400 shows a variety of data for a particular billing code (e.g., "99284") from the chargemaster analysis system 100. For example, the billing code summary user interface 1400 may include a billing code findings area 1402, a since last detected CMI area 1404, a contract information area 1406, a detection details area 1408, and a claims data area 1410.

The billing code findings area 1402 can identify the detected CMI percentage, a data cleanliness value, the date of surveillance, and the detected CMI date for the selected billing code. The since last detected CMI area 1404 can identify various data regarding the billing code since the last detected CMI including the total charges, the total charge change impact, the amount allowed to enforce, and the percentage of billing codes included in the aggregation.

The contract information area 1306 can identify the CPL, the current contract effective date, and the next contract effective date for the provider, category, sub-category, and/or billing code. The detection details area 1408 can identify the number of claimlines, the number of valid changepoints, the number of spikes, and the number of units at the billing code level.

The claims data area 1410 can display historical price data for the selected billing code. The historical price data can be shown as a time-series graph 1412 of how the selected billing code has been billed by a selected provider over a period of time. An operator may use a text entry box or a dropdown menu 1414 to select the period of time displayed in the time-series graph 1412. An operator may also use a text entry box or a dropdown menu 1416 to select whether to display filtered data or unfiltered data in the time-series graph 1412.

The time-series graph 1412 may shows a line chart 1418 of claimline charges in the historical price data. In some embodiments, the time-series graph 1412 may also show any price spikes 1420 in the historical price data. The time-series graph 1412 can also show an indicia 1422 (e.g., a vertical line) indicating the date that a CMI has been detected by the chargemaster analysis system 100. The time-series graph 1412 can also show an indicia 1424 (e.g., a horizontal line) indicating the mode unit charge of the billing code before the CMI.

FIGS. 15-18 are example data tables showing data from the output data store 116. FIG. 15 is an example of the filtered claimline data 126 shown as a filtered claimline data table 1500. In some embodiments, the filtered claimline data table 1500 may be presented in a user interface by the user device 134 to an operator. The filtered claimline data table 1500 may include various data on one or more claimlines. Each row represents a different claimline. Each column displays an attribute of the claimline. The filtered claimline data table 1500 may include a provider category code ID 1502, a provider ID 1504, a category ID 1506, a code ID 1508, a date of the claimline 1510, a charge of the claimline 1512, a unit count 1514, a billed per unit amount (raw) 1516, an allowed amount 1518, a billed per unit (rounded) 1520, a billed per unit (filtered) 1522, and a spike flag 1524 for the displayed one or more claimlines. The provider category code ID may be a concatenation of the provider ID 1504, the category ID 1506, and the code ID 1508. The provider ID 1504 is the identification code for the particular provider. The category ID 1506 can identify the service category. The code ID 1508 identifies the billing code. The date of the claimline 1510 is the date the billing code in the claimline was rendered. The charge in the claimline 1512 is the charge for the billing codes in the claimline. The unit count 1514 is the number of billing code units in the claimline. The billed per unit (raw) 1516 is equal to the charge of the claimline 1512 pulled from the claimline data 122. The billed per unit (raw) may be preprocessed as described above to generate the billed per unit. The allowed amount 1518 is the maximum amount for the billing code that the insurer will pay under the contract with the provider. The billed per unit (rounded) 1520 is the equal to the billed per unit raw (1516) after rounding values greater than $10 to the nearest dollar. The billed per unit (filtered) 1522 is equal to the billed per unit field with spike values replaced with corrected values. The spike flag 1524 is a Boolean field indicating whether a changepoint is a spike. If the spike flag 1524 is true, then the billed per unit (filtered) 1522 is different than the billed per unit (raw) 1516.

FIG. 16 is an example of multi-level metric data 130 shown as a code-level metric data table 1600. In some embodiments, the code-level metric data table 1600 may be presented in a user interface by the user device 134 to an operator. The code-level metric data table 1600 may include various data on one or more billing codes. Each row represents a different billing code. Each column displays an attribute of the billing code. The code-level metric data table 1600 may include the same fields as the filtered claimline data table 1500, such as the provider category code ID 1502, the provider ID 1504, the category ID 1506, the code ID 1508, and the unit count. The code-level metric data table 1600 may also include a last CMI date 1602, a data cleanliness value 1604, a number of claimlines 1606, a number of changepoints 1608, a number of spikes 1610, a mode of unit charge before the CMI 1612, a mode of unit charge after the CMI 1614, a percent increase at the CMI 1616, a total charge 1618, a total allowed amount 1620, and a charge change since the CMI 1622 for the displayed one or more billing codes. The last CMI date 1602 is the date of the last CMI. The data cleanliness value 1604 is the data cleanliness value calculated at 320 described above with respect to FIG. 3. The number of claimlines 1606 is the number of claimlines in which the billing code appears. The number of changepoints 1608 is the number of changepoints for the billing code. The mode of the unit charge before the CMI 1612 and the mode of the unit charge after the CMI 1614 are the modes of the unit charges of the billing code before and after the CMI date, respectively. The percent increase at CMI 1616 is the percent increase in the price of the billing code at the CMI date. The total charge 1618 is the total charge for the billing code. The total allowed amount 1620 is the maximum amount for the billing code that the insurer will pay under the contract with the provider. The charge change since the CMI 1622 is equal to the difference between the mode of the unit charge after the CMI 1614 and the mode of the unit charge before the CMI 1612 multiplied by the unit count 1514 (e.g., (468−427)×3=123).

FIG. 17 is an example of the changepoint data 128 shown as a changepoint data table 1700. In some embodiments, the changepoint data table 1700 may be presented in a user interface by the user device 134 to an operator. The changepoint data table 1700 may include various data on one or more claimlines. Each row represents a different claimline. Each column displays an attribute of the claimline. The changepoint data table 1700 may include the same fields as the filtered claimline data table 1500, such as the provider category code ID 1502, the provider ID 1504, the category ID 1506, the code ID 1508, the date of the claimline 1510, the charge of the claimline 1512, the unit count 1514, the billed per unit amount (raw) 1516, the allowed amount 1518, the billed per unit (rounded) 1520, the billed per unit (filtered) 1522, and the spike flag 1524 for the displayed one or more claimlines. The changepoint data table 1700 may also include a difference from the baseline 1702, a difference from the baseline (no spikes) 1704, and a changepoint type 1706. The changepoint data table 1700 may also include a last CMI date 1708 similar to 1602 in FIG. 16. The difference from the baseline 1702 is the difference in the price at the changepoint and the baseline price of the billing code. The difference from the baseline (no spiked) 1702 is the difference in the price at the changepoint and the baseline price of the billing code for valid changepoints and is set to zero (0) if the changepoint is a spike. The changepoint type 1706 identifies the changepoint as valid, spike, or repeat.

FIG. 18 is an example of the alert data 132 shown as an alert data table 1800. In some embodiments, the alert data table 1800 may be presented in a user interface by the user device 134 to an operator. The alert data table 1800 may include various data on one or more providers. Each row represents a different provider. Each column displays an attribute of the data associated with the provider. The alert data table 1800 may include a provider ID column 1504, a surveillance date column 1802, an alert type column 1804, a CMI date column 1806, a data cleanliness value column 1808, a claimlines number column 1810, a changepoints number column 1812, a spike number column 1814, a unit count column 1816, a total charge column 1818, a charge change since the CMI column 1820, and a provider CMI percent increase column 1822 for the displayed one or more providers.

The column 1802 is the date that the surveillance was conducted by the chargemaster analysis system 100 to identify whether a CMI had occurred. The column 1804 identifies the type of alert (e.g., a monthly increase alert). Although a monthly increase alert is shown, the alert data 132 may include other alert data and that the alert module 110 can build and publish other alert types. The column 1806 is the date that a CMI was detected. The column 1808 is the data cleanliness value of the claimlines calculated at 320 described above with respect to FIG. 3.

The column 1810 indicates the number of claimlines identified during the surveillance. The column 1812 indicates the number of claimlines identified during the surveillance. The column 1814 indicates the number of spikes in prices of billing codes identified during the surveillance. The column 1816 indicates the number of units identified during the surveillance. The column 1818 indicates the charge for the provider since the CMI. The column 1820 indicates the total increase in charges for the provider since the last CMI date. The column 1822 indicates the total percent increase in charges for the provider since the last CMI date.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. In the written description and claims, one or more steps within a method may be executed in a different order (or concurrently) without altering the principles of the present disclosure. Similarly, one or more instructions stored in a non-transitory computer-readable medium may be executed in different order (or concurrently) without altering the principles of the present disclosure. Unless indicated otherwise, numbering or other labeling of instructions or method steps is done for convenient reference, not to indicate a fixed order.

Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. The phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are IEEE Standard 802.15.4 (including the ZIGBEE standard from the ZigBee Alliance) and, from the Bluetooth Special Interest Group (SIG), the BLUETOOTH wireless networking standard (including Core Specification versions 3.0, 4.0, 4.1, 4.2, 5.0, and 5.1 from the Bluetooth SIG).

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module. For example, the client module may include a native or web application executing on a client device and in network communication with the server module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A computerized analysis system for automated anomaly identification, the system comprising:
   processor hardware; and
   memory hardware configured to store instructions that, when executed by the processor hardware, cause the processor hardware to perform operations, wherein the operations include:

operating the system at a large scale by retrieving claimline data for a period of time from an input data store, wherein the claimline data includes a plurality of billing codes and prices of the plurality of billing codes associated with a provider,
  wherein the large scale includes at least 10,000 records;
flagging and filtering anomalous price spikes in the claimline data;
determining whether a changepoint exists in the plurality of billing codes in the claimline data;
identifying a chargemaster increase for the provider in response to a statistical parameter of changepoints exceeding a threshold; and
in response to identification of the chargemaster increase, publish publishing an alert that the chargemaster increase has occurred for the provider.

2. The system of claim 1, wherein the operations include:
creating a user interface for display to a user based on the alert; and
creating the user interface via a web server.

3. The system of claim 1, wherein the operations include:
setting n=1;
creating a time series of billing codes from the claimline data;
selecting a data point of the time series, wherein the selected data point is not the second to last data point of the time series;
flagging the selected data point as a spike in response to a determination that the selected data point is not equal to any of:
  an n earlier data point of the time series;
  an n later data point of the time series;
  an n+1 earlier data point of the time series; and
  an n+1 later data point of the time series; and
copying the selected data point to a filtered claimline data in response to a determination that the selected data point is equal to any one of:
  the n earlier data point of the time series;
  the n later data point of the time series;
  the n+1 earlier data point of the time series; and
  the n+1 later data point of the time series.

4. The system of claim 3, wherein the time series includes:
the last two data points of an initial time series of billing codes from the claimline data from a period of time immediately prior to the period of time; and
the data points of an initial time series of billing codes from the claimline data for the period of time.

5. The system of claim 4, wherein the operations include classifying the last data point in the initial time series of billing codes from the claimline data from the prior period of time in response to a determination that the last data point is not equal to:
the second to last data point in the initial time series of billing codes from the claimline data from the prior period of time; and
the first data point in the initial time series of billing codes from the claimline data for the period of time.

6. The system of claim 1, wherein the operations include:
setting n=1;
creating a time series of billing codes from the claimline data;
selecting a data point of the time series, wherein the selected data point is the second to last data point of the time series for the period of time;
flagging the selected data point as a spike in response to a determination that the selected data point is not equal to any of:
  an n earlier data point of the time series;
  an n later data point of the time series; and
  an n+1 earlier data point of the time series; and
copying the selected data point to a filtered claimline data in response to a determination that the selected data point is equal to any one of:
  the n earlier data point of the time series;
  the n later data point of the time series; and
  the n+1 earlier data point of the time series.

7. The system of claim 6, wherein the time series includes:
the last two data points of an initial time series of billing codes from the claimline data for a period of time immediately prior to the period of time; and
the data points of an initial time series of billing codes of the claimline data for the period of time.

8. The system of claim 7, wherein the operations include classifying the last data point in the initial time series of billing codes from the claimline data from the prior period of time in response to a determination that the last data point is not equal to:
the second to last data point in the initial time series of billing codes from the claimline data from the prior period of time; and
the first data point in the initial time series of billing codes from the claimline data for the period of time.

9. The system of claim 1, wherein the operations include:
obtaining historical changepoint data from an output data store;
obtaining historical claimline data since a last chargemaster increase; and
determining a baseline price for each billing code.

10. The system of claim 1, wherein the alert includes at least one of:
an identification of the provider;
a chargemaster increase date;
a number of claimlines;
a number of changepoints;
an identification of the billing code; and
a price of the billing code at the changepoint.

11. The system of claim 1, wherein the operations include enforcing a chargemaster cap.

12. The system of claim 11, wherein the operations include, in response to publication of an alert:
extracting a discount corresponding to the billing code from a contract with the provider, where the contract is stored in the input data store;
extracting a cap corresponding to the billing code from the contract;
calculating a percent increase of the price of the billing code at the changepoint compared to a baseline price for the billing code;
in response to a determination that the percent increase of the price of the billing code at the changepoint is greater than the cap, calculating an adjusted discount for the billing code; and
creating a new contract having the adjusted discount.

13. A computerized method comprising:
performing anomaly detection at a large scale by retrieving claimline data for a period of time from an input data store, wherein the claimline data includes a plurality of billing codes and prices of the plurality of billing codes associated with a provider,
  wherein the large scale includes at least 10,000 records;

creating a time series of billing codes from the claimline data;
selecting a data point of the time series, wherein the selected data point is not the second to last data point of the time series;
flagging the selected data point as a spike in response to a determination that the selected data point is not equal to one or more preceding data points of the time series or one or more subsequent data points of the time series;
copying the selected data point to a filtered claimline data in response to a determination that the selected data point is equal to one or more preceding data points of the time series or one or more subsequent data points of the time series;
determining whether a changepoint exists in the plurality of billing codes in the claimline data;
in response to determining that the changepoint exists, classifying the changepoint;
identifying a chargemaster increase for the provider in response to a statistical parameter of changepoints exceeding a threshold;
in response to identification of the chargemaster increase, publishing an alert that the chargemaster increase has occurred for the provider; and
creating a user interface for display to a user, wherein the user interface includes the alert.

14. The method of claim 13, further comprising:
classifying the last data point in an initial time series of billing codes from the claimline data for a period of time immediately prior to the period of time in response to a determination that the last data point is not equal to:
the second to last data point in the initial time series of billing codes from the claimline data from the prior period of time; and
the first data point in an initial time series of billing codes from the claimline data for the period of time.

15. The method of claim 13, further comprising:
obtaining historical changepoint data from an output data store;
obtaining historical claimline data since a last chargemaster increase; and
determining a baseline price for each billing code.

16. The method of claim 13, further comprising:
in response to determining that the changepoint exists, classifying the changepoint as one of a spike, a repeat, and a valid changepoint.

17. The method of claim 13, further comprising:
in response to determining that the changepoint exists, appending the changepoint to an output data store.

18. The method of claim 13, further comprising, in response to publication of the alert:
extracting a discount corresponding to the billing code from a contract with the provider, where the contract is stored in the input data store;
extracting a cap corresponding to the billing code from the contract;
calculating a percent increase of the price of the billing code at the changepoint compared to a baseline price for the billing code;
in response to a determination that the percent increase of the price of the billing code at the changepoint is greater than the cap, calculating an adjusted discount for the billing code; and
creating a new contract with the provider having the adjusted discount.

19. A non-transitory computer-readable medium storing processor-executable instructions, the instructions comprising:
operating a system for automatic anomaly identification at a large scale by obtaining claimline data of a provider for a period of time from an input data store, wherein the large scale includes at least 10,000 records;
identifying a billing code in the claimline data for a selected month;
creating a time series of prices for the billing code by aggregating same-day billing code prices in the claimline data for the selected month;
selecting a data point of the time series for the selected month;
flagging the selected data point as a spike in response to a determination that the selected data point is not equal to one or more preceding data points of the time series or one or more subsequent data points of the time series;
copying the selected data point to a filtered claimline data in response to a determination that the selected data point is equal to one or more preceding data points of the time series or one or more subsequent data points of the time series; and
in response to one or more of flagging the selected data point as a spike, generating an indicia for display to a user in a user interface that indicates that the price of the billing code of the selected data point is a spike.

20. The computer-readable medium of claim 19, wherein the instructions include:
determining a baseline price for the billing code;
comparing a price for the billing code in the time series to the baseline price to determine a changepoint;
for each day of the selected month, counting a total number of changepoints;
determining a statistical parameter of changepoints per day throughout the selected month;
determining whether a maximum number of changepoints on any given day exceeds the statistical parameter of changepoints per day by a threshold;
in response to determining that the maximum number of changepoints exceeds the statistical parameter of changepoints per day by the threshold, selecting the day of the month with the maximum number of changepoints; and
identifying a chargemaster increase for the selected day.

* * * * *